(12) United States Patent
Koffler et al.

(10) Patent No.: US 12,364,609 B2
(45) Date of Patent: Jul. 22, 2025

(54) BIOMIMETIC IMPLANTS

(71) Applicant: THE REGENTS OF THE UNIVERSITY OF CALIFORNIA, Oakland, CA (US)

(72) Inventors: Yacov Koffler, La Jolla, CA (US); Shaochen Chen, La Jolla, CA (US); Mark Tuszynski, La Jolla, CA (US); Wei Zhu, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1023 days.

(21) Appl. No.: 16/468,586

(22) PCT Filed: Dec. 12, 2017

(86) PCT No.: PCT/US2017/065857
§ 371 (c)(1),
(2) Date: Jun. 11, 2019

(87) PCT Pub. No.: WO2018/111900
PCT Pub. Date: Jun. 21, 2018

(65) Prior Publication Data
US 2019/0350720 A1 Nov. 21, 2019

Related U.S. Application Data

(60) Provisional application No. 62/433,142, filed on Dec. 12, 2016.

(51) Int. Cl.
*A61F 2/02* (2006.01)
*A61F 2/30* (2006.01)
(Continued)

(52) U.S. Cl.
CPC ............ *A61F 2/44* (2013.01); *A61F 2/30771* (2013.01); *A61F 2/30942* (2013.01);
(Continued)

(58) Field of Classification Search
None
See application file for complete search history.

(56) References Cited

U.S. PATENT DOCUMENTS

| 5,092,871 A | 3/1992 | Aebischer |
| 5,370,681 A | 12/1994 | Herweck |

(Continued)

FOREIGN PATENT DOCUMENTS

| CN | 102166140 A | 8/2011 |
| EP | 3241524 A1 | 11/2017 |

(Continued)

OTHER PUBLICATIONS

Koffler et al. "Biomimetic 3-D printed scaffolds for spinal cord injury repair," Nature Medicine 25:263-269, https://doi.org/10.1038/s41591-018-0296-z, 2019.
(Continued)

*Primary Examiner* — Ann Schillinger
(74) *Attorney, Agent, or Firm* — PERKINS COIE LLP

(57) ABSTRACT

Implantable devices for spinal cord and peripheral nerve injury are described. The implants include a three-dimensional printed structure having stem cells disposed therein. Also disclosed are methods of treating neuronal injuries with the disclosed implants.

20 Claims, 35 Drawing Sheets

(51) Int. Cl.
  *A61F 2/44* (2006.01)
  *A61L 27/18* (2006.01)
  *A61L 27/38* (2006.01)
  *A61L 27/56* (2006.01)

(52) U.S. Cl.
  CPC ....... *A61L 27/3834* (2013.01); *A61L 27/3856* (2013.01); *A61L 27/3878* (2013.01); *A61F 2002/30062* (2013.01); *A61F 2002/30784* (2013.01); *A61F 2002/30838* (2013.01); *A61F 2002/30985* (2013.01); *A61F 2002/4495* (2013.01); *A61L 2430/38* (2013.01)

(56) References Cited

U.S. PATENT DOCUMENTS

| | | | |
|---|---|---|---|
| 5,925,053 | A | 7/1999 | Hadlock |
| 6,337,198 | B1 | 1/2002 | Levene et al. |
| 6,676,675 | B2 | 1/2004 | Mallapragada |
| 6,716,225 | B2 | 4/2004 | Li |
| 8,075,904 | B2 | 12/2011 | Sakamoto |
| 8,246,680 | B2 | 8/2012 | Betz et al. |
| 8,275,594 | B2 | 9/2012 | Lin et al. |
| 8,728,817 | B2 | 5/2014 | Ogle et al. |
| 8,926,886 | B2 | 1/2015 | Pandit |
| 9,555,583 | B1 * | 1/2017 | Dirk ................. B33Y 10/00 |
| 9,585,666 | B2 | 3/2017 | Yu |
| 9,968,705 | B2 * | 5/2018 | Christ ................. C12N 5/0658 |
| 10,426,872 | B2 * | 10/2019 | Sakamoto ............ A61L 27/34 |
| 11,110,207 | B2 * | 9/2021 | Sakamoto ............ A61L 27/34 |
| 2003/0039676 | A1 * | 2/2003 | Boyce .................. A61F 2/32 623/16.11 |
| 2003/0040112 | A1 * | 2/2003 | Muir ................. A61L 31/047 435/368 |
| 2004/0037813 | A1 * | 2/2004 | Simpson ............. A61L 15/32 424/443 |
| 2004/0220672 | A1 | 11/2004 | Shadduck |
| 2005/0113923 | A1 | 5/2005 | Acker et al. |
| 2006/0002978 | A1 * | 1/2006 | Shea .................. A61L 27/54 514/8.4 |
| 2006/0136182 | A1 | 6/2006 | Vacanti et al. |
| 2007/0010831 | A1 | 1/2007 | Romero-Ortega |
| 2007/0259020 | A1 | 11/2007 | Langer et al. |
| 2008/0125870 | A1 | 5/2008 | Carmichael et al. |
| 2010/0047310 | A1 | 2/2010 | Chen |
| 2010/0068240 | A1 * | 3/2010 | Chiu .................. A61K 38/1825 514/777 |
| 2011/0032139 | A1 | 3/2011 | Bowlin |
| 2011/0245852 | A1 * | 10/2011 | Downes ............... A61L 27/56 156/218 |
| 2011/0313542 | A1 | 12/2011 | Forgacs |
| 2012/0221025 | A1 | 8/2012 | Simpson et al. |
| 2012/0276068 | A1 | 11/2012 | Sabaawy |
| 2012/0330423 | A1 | 12/2012 | Lin et al. |
| 2013/0096685 | A1 | 4/2013 | Ciupik et al. |
| 2013/0344601 | A1 * | 12/2013 | Soman ................ A61L 27/14 264/401 |
| 2014/0017284 | A1 * | 1/2014 | Yang .................. A61K 35/35 623/23.72 |
| 2015/0023911 | A1 * | 1/2015 | Schilling ............ C12N 5/0641 435/375 |
| 2015/0202351 | A1 * | 7/2015 | Kaplan ................ A61B 5/6877 607/116 |
| 2016/0067375 | A1 | 3/2016 | Holmes |
| 2016/0129155 | A1 | 5/2016 | Lin et al. |
| 2018/0280580 | A1 | 10/2018 | Sakamoto et al. |

FOREIGN PATENT DOCUMENTS

| | | | |
|---|---|---|---|
| JP | 2015-89433 | A | 5/2015 |
| WO | 2007127790 | A2 | 11/2007 |
| WO | 2011/032139 | A2 | 3/2011 |
| WO | 2011097330 | A2 | 8/2011 |
| WO | 2013040087 | A2 | 3/2013 |
| WO | 2013058670 | A | 4/2013 |
| WO | WO-2015103149 | A1 * | 7/2015 ............... A61F 2/28 |
| WO | 2016077830 | A1 | 5/2016 |
| WO | 2016077839 | A1 | 5/2016 |
| WO | 2017/062845 | A1 | 7/2017 |
| WO | 2018/111900 | A1 | 6/2018 |
| WO | 2018/144135 | A1 | 8/2018 |
| WO | 2020/146658 | A2 | 7/2020 |

OTHER PUBLICATIONS

Laporte et al. :Vascular endothelial growth factor and fibroblast growth factor 2 delivery from spinal cord bridges to enhance angiogenesis following injury, J Biomed Mater Res Part A 98A:372-382, 2011.
Laporte et al. "Plasmid releasing multiple channel bridges for transgene expression after spinal cord surgery," Molecular Therapy 17:318-326, 2009.
Laporte et al. "Local gene delivery from ECM coated poly(lactide-co-glycolide) multiple channel bridges after spinal cord surgery," Biomaterials 30:2361-2368, 2009.
Yang et al. "Multiple Channel Bridges for Spinal Cord Injury: Cellular Characterization of Host Response," Tissue Engineering: Part A 15:2383-2395, 2009.
IP Australia, Notice of Acceptance for Patent Application No. 2017375956 dated May 15, 2023, 3 pages.
Japan Patent Office, Translation of Notification of Reasons for Rejection for Japanese Patent Application No. 2022-163769 dated Sep. 5, 2023, 6 pages.
IP Office Canada, Office Action for Canadian Application No. 3,046,959, mailed on May 1, 2024.
EPO, Summons to Oral Proceedings for European Application No. 17882172.4, mailed on Jul. 18, 2024, 6 pages.
Fairbanks, B.D. et al., "Photoinitiated polymerization of PEG-diacrylate with lithium phenyl-2,4,6-trimethylbenzoylphosphinate: polymerization rate and cytocompatibility", Biomaterials 30:6702-6707, 2009.
Hu et al., "3D-engineering off Cellularized Conduits for Peripheral Nerve Regeneration," Scientific Reports, 2016, 6:32184, 1-12.
Lu, P. et al."Long-distance growth and connectivity of neural stem cells after severe spinal cord injury" , Cell 150:1264-1273, 2012.
Murphy et al,"Understanding the effect of mean pore size on cell activity in collagen-glycosaminoglycan scaffolds," Cell Adhesion and Migration 4:3, 377-381, 2010.
Soman, P. et al., "Digital microfabrication of user-defined 3D microstructures in cell-laden hydrogels", Biotechnol Bioeng 110:3038-3047, 2013.
IP Office Australia, Exam Report No. 1 for Australian Application No. 2017375956, mailed on Jun. 10, 2022, 3 pages.
CNIPA, First Office Action for Chinese Application No. 201780083831.1, mailed on Apr. 27, 2021, 19 pages with English translation.
CNIPA, Second Office Action for Chinese Application No. 201780083831.1, mailed on Nov. 25, 2021, 8 pages with English translation.
CNIPA, Third Office Action for Chinese Application No. 201780083831.1, mailed on Jul. 4, 2022, 9 pages English machine translation.
CNIPA, Fourth Office Action for Chinese Application No. 201780083831.1, mailed on Mar. 31, 2023, 10 pages with English translation.
CNIPA, Fifth Office Action for Chinese Application No. 201780083831.1, mailed on Aug. 24, 2023, 14 pages with English translation.
CNIPA, Rejection Decision for Chinese Application No. 201780083831.1, mailed on Jan. 29, 2024, 14 pages with English translation.
EPO, Extended European Search Report for European Application No. 17882172.4, mailed on Jul. 8, 2020, 6 pages.
EPO, Communication pursuant to Article 94(3) EPC for European Application No. 17882172.4, mailed on Jul. 21, 2021, 6 pages.
EPO, Communication pursuant to Article 94(3) EPC for European Application No. 17882172.4, mailed on Mar. 27, 2023, 5 pages.
EPO, Extended European Search Report and Opinion for European Application No. 20788207.7, mailed on Nov. 25, 2022, 8 pages.
JPO, Search Report for Japanese Application No. 2019-551919, mailed on Oct. 20, 2021, 19 pages with English translation.

(56) References Cited

OTHER PUBLICATIONS

JPO, Notice of Reasons for Refusal for Japanese Application No. 2019-551919, mailed on Nov. 16, 2021, 10 pages with English translation.
JPO, Decision to Grant a Patent for Japanese Application No. 2019-551919, mailed on Sep. 13, 2022, 6 pages with English translation.
JPO, Written Opinion for Japanese Application No. 2019-551919, mailed on Apr. 22, 2022, 8 pages with English translation.
JPO, Written Opinion for Japanese Application No. 2022-163769, mailed on Mar. 4, 2024, 7 pages with English translation.
JPO, Notice of Reasons for Refusal for Japanese Application No. 2022-163769, mailed on May 9, 2024, 7 pages.
JPO, Notice of Reasons for Refusal for Japanese Application No. 2021-559949, mailed on Dec. 5, 2023, 11 pages with English translation.
JPO, Notice of Reasons for Refusal for Japanese Application No. 2021-559949, mailed on Jun. 25, 2024, 11 pages with English translation.
KIPO, Office Action for Korean Application No. 10-2019-7020450, mailed on Sep. 17, 2022, 5 pages (English translation)
KIPO, Written Opinion for Korean Application No. 10-2019-7020450, mailed on Mar. 16, 2023, 25 pages with English translation.
KIPO, Written Decision on Registration for Korean Application No. 10-2019-7020450, mailed on Jul. 27, 2023, 6 pages with English translation.
ISA/US, International Search Report and Written Opinion for International Application No. PCT/US2017/065857, mailed on Mar. 6, 2018, 12 pages.
ISA, International Search Report and Written Opinion for International Application No. PCT/US2020/027773, mailed on Jun. 19, 2020, 9 pages.
Intellectual Property India, First Examination Report for Indian Application No. 202117049666, mailed on Aug. 9, 2024.
Zhu, W. et al. "Rapid continuous 3D printing of customizable peripheral nerve guidance conduits," Mater Today, 21 951-959, 2018.
USPTO, Nonfinal Office Action for U.S. Appl. No. 17/602,727, mailed on Jun. 5, 2024, 16 pages.
USPTO, Final Office Action for U.S. Appl. No. 17/602,727, mailed on Dec. 5, 2024, 16 pages.
USPTO, Advisory Action for U.S. Appl. No. 17/602,727, mailed on Feb. 20, 2025, 9 pages.
JPO, Decision of Rejection for Japanese Application No. 2022-163769, mailed on Dec. 10, 2024, 4 pages with unofficial English translation.
JPO, Decision of Rejection for Japanese Application No. 2021-559949, mailed on Jan. 21, 2025, 14 pages with machine English translation.
Shahriari et al., "Peripheral nerve growth within a hydrogel microchannel scaffold supported by a kink-resistant conduit," J Biomed Mater Res Part A, 2017, vol. 105A, pp. 3392-3399.
Srinivasan et al., "Microchannel-based regenerative scaffold for chronic peripheral nerve interfacing in amputees," Biomaterials, 2014, vol. 41, 34 pages.
CIPO, Examiner's Report for Canadian Application No. 3,136,330, mailed on Mar. 20, 2025, 5 pages.
USPTO, Non-Final Office Action for U.S. Appl. No. 17/602,727, mailed on Apr. 11, 2025, 22 pages.
CNIPA, Office Action for Chinese Application No. 202080036615.3, mailed on Mar. 11, 2025, 27 pages including translation.

\* cited by examiner

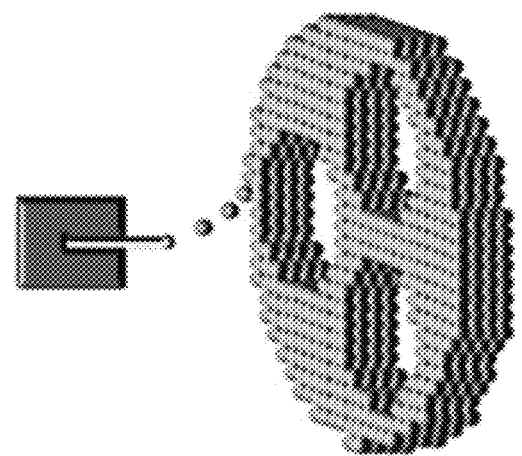
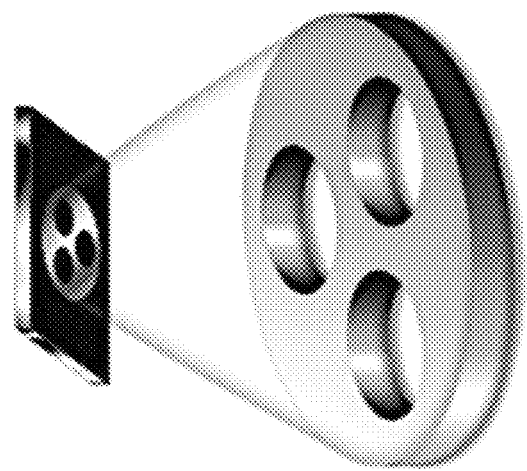
FIG. 1B
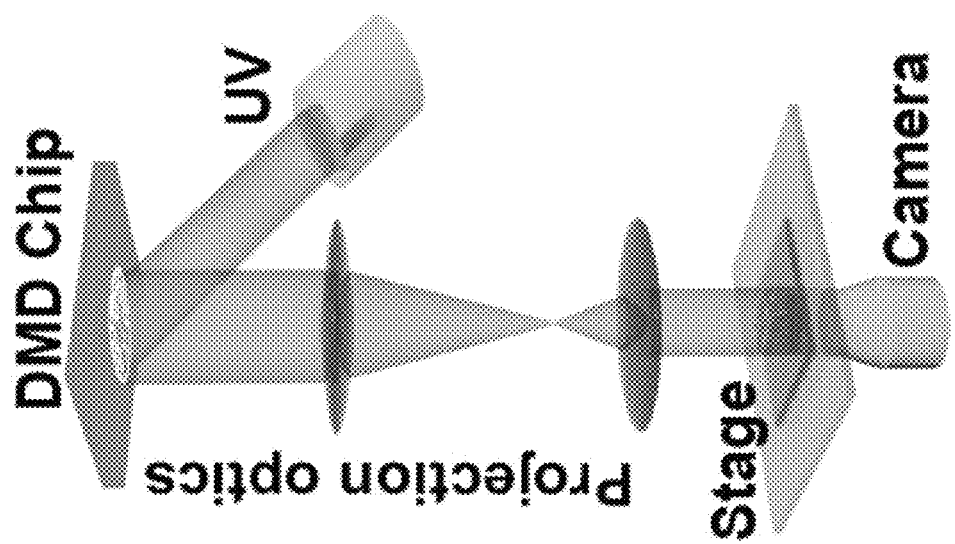
FIG. 1A

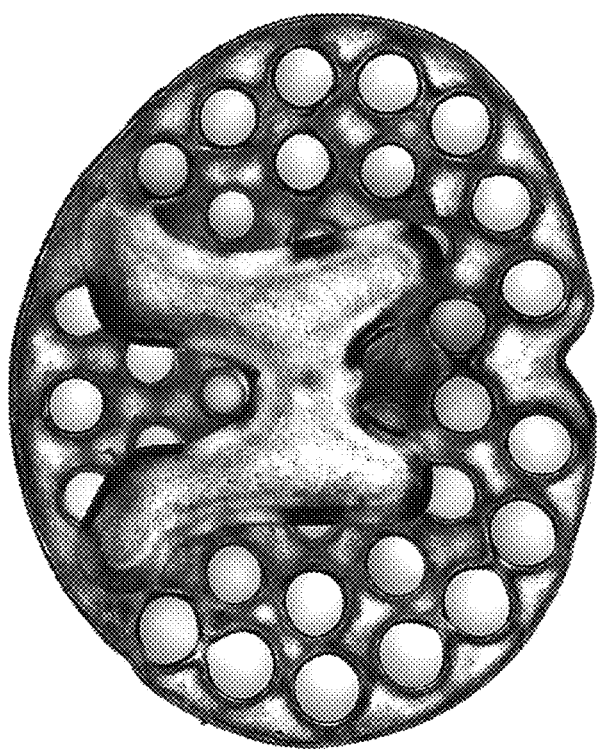
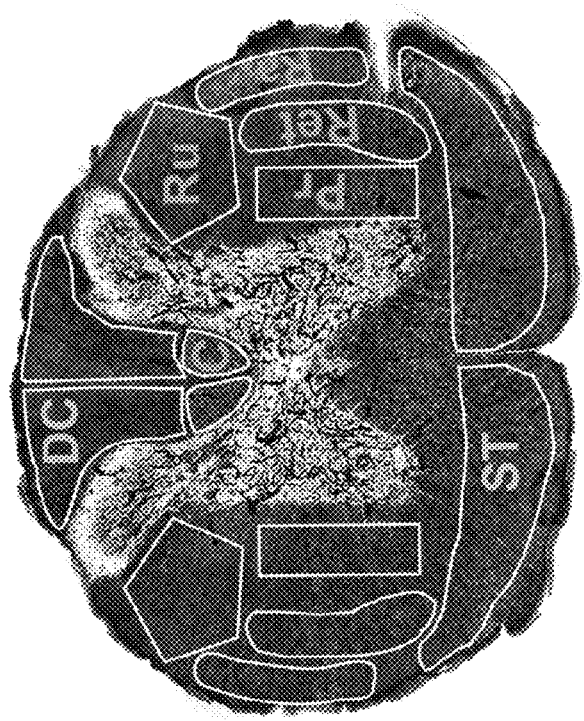
FIG. 1D

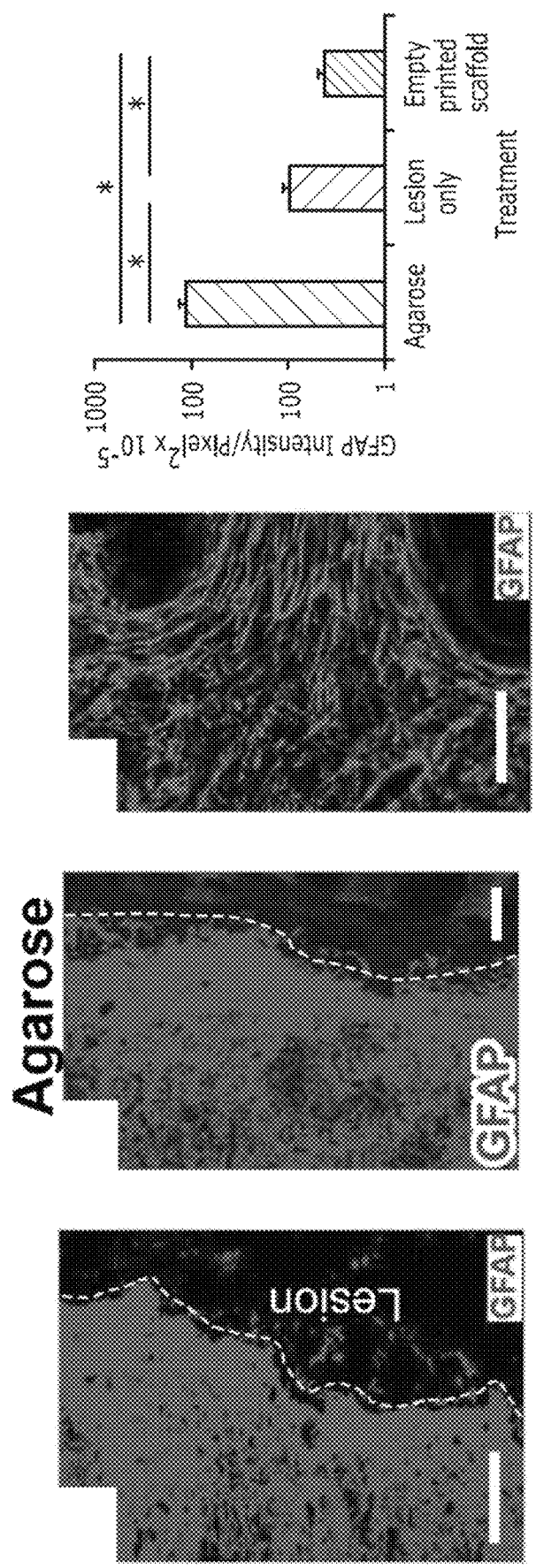

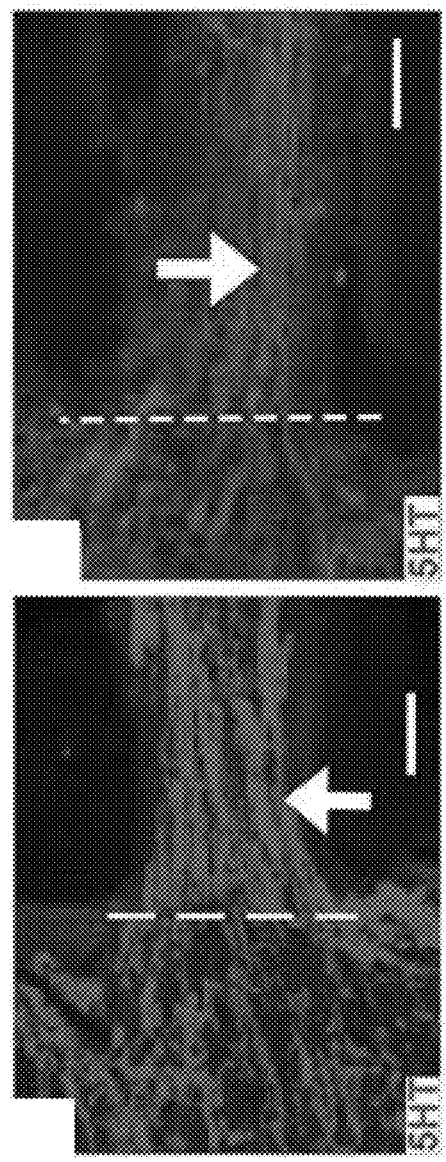

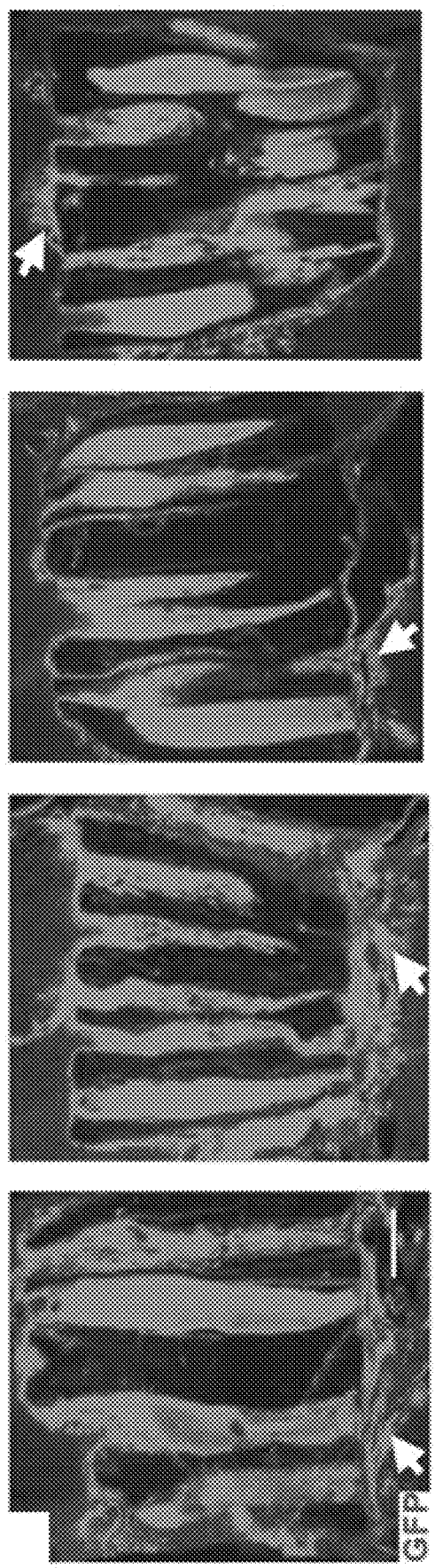

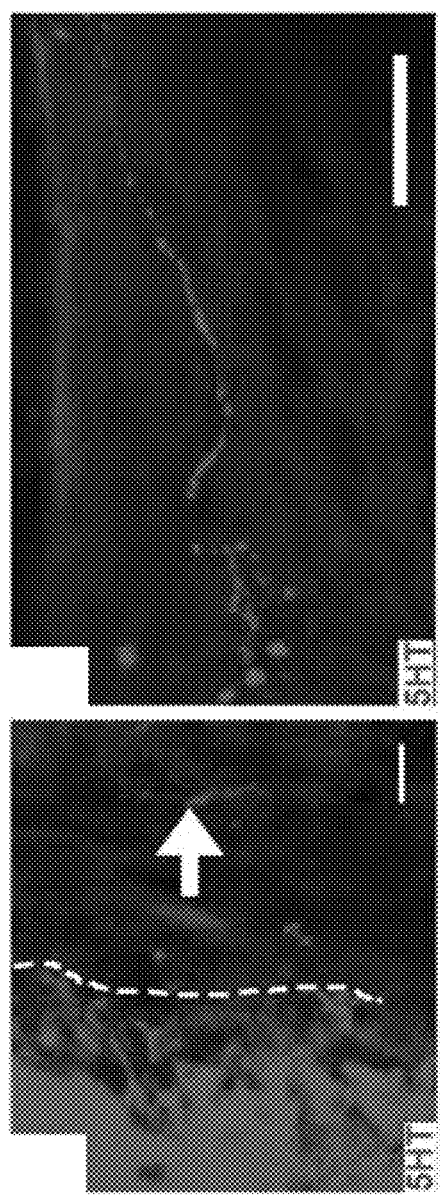
*FIG. 24A*
*FIG. 23*
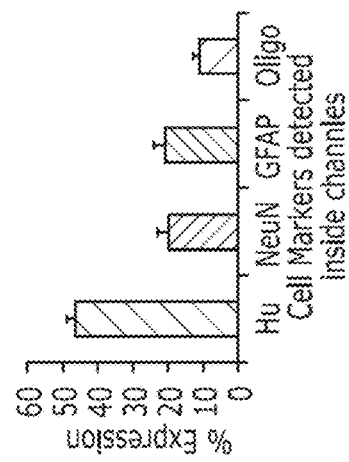
*FIG. 22*

BIOMIMETIC IMPLANTS

CROSS REFERENCE TO RELATED APPLICATIONS

This application is a national phase of International Patent Application PCT/US2017/065857 filed Dec. 12, 2017, which claims the benefit of U.S. Provisional Application No. 62/433,142 filed Dec. 12, 2016, both of which are incorporated herein by reference in their entireties.

STATEMENT REGARDING FEDERALLY SPONSORED RESEARCH OR DEVELOPMENT

This invention was made with Government support under Grant No. EB014986, awarded by the National Institutes of Health. The Government has certain rights in this invention.

FIELD

Disclosed herein are three dimensional biomimetic implants containing stem cells for treatment of spinal cord and peripheral nerve injuries

BACKGROUND

Methods for bioprinting functional tissue have faced many challenges, among which is lack of appropriate biofabrication techniques to build complex three-dimensional (3D) microarchitectures essential for guiding cell growth and promoting tissue maturation. Three-dimensional printing of central nervous system structures has not been successfully accomplished previously.

SUMMARY

Described herein are implantable devices or implants for tissue repair. In some embodiments, the tissue can be spinal cord tissue or peripheral nerve tissue. These implants can be used to treat injury to either of these types of tissues.

The implants can include a three-dimensional printed structure without layers. In some embodiments, the implant can include the three-dimensional printed structure including a first end and a second end, one or more channels originating at the first end and terminating at the second end, and at least one type of stem cell included in the at least one channel.

In some embodiments, the implant is biomimetic. The implant can be biomimetic to a spinal cord and include a core (representing the spinal cord gray matter) and a shell (representing the spinal cord white matter), wherein the shell contains channels. In other embodiments, the implant can be biomimetic to a peripheral nerve and include a honeycomb structure of linear channels packed together. In cases of spinal cord or peripheral nerve, the linear channels can guide regenerating axons to another side of a lesion.

Thus, disclosed herein are biomimetic implants for spinal cord or peripheral nerve injury, the implant comprising: a three-dimensional (3D) implant including a first end and a second end and comprising a core and a shell and mimicking the structure of the injury site, at least one channel in the shell originating at the first end and terminating at the second end, and at least one type of stem cell included in the at least one channel.

In some embodiments, the implant is produced by 3D printing.

In some embodiments, the at least one type of stem cell is a neural stem cell. In some embodiments, the neural stem cell is an embryonic stem cell, an iPSC derived stem cell, a directly differentiated neural stem cell, or a combination thereof. In some embodiments, the at least one type of stem cell is a mesenchymal stem cell. In some embodiments, the stem cell is engineered to express BDNF, NT3, GDNF, or a combination thereof.

In some embodiments, the three-dimensional printed implant includes polyethylene glycol diacrylate, or gelatin methacrylol, or a combination thereof.

In some embodiments, the implant is biomimetic to a spinal cord. In some embodiments, the implant is biomimetic to a peripheral nerve.

In some embodiments, the channels are linear. In some embodiments, the channels are parallel to each other. In some embodiments, the channels guide regenerating axons from the first end to the second end. In some embodiments, the implant includes two or more channels having hexgaonal cross-sections clustered as a honeycomb structure.

Also disclosed herein are methods for treating a neurological injury in a host in need thereof, the method comprising: implanting a biomimetic implant disclosed herein into a location needing treatment; and allowing regeneration of cells at the injury site.

In some embodiments, the neurological injury is a spinal cord injury, a motor complete spinal cord injury, a motor incomplete spinal cord injury, or a peripheral nerve injury. In some embodiments, the neurological injury is spinal cord injury. In some embodiments, the neurological injury is peripheral nerve injury.

In some embodiments, the method further comprising providing physical therapy to the host.

Also disclosed herein are methods of fabricating a biomimetic implants as disclosed herein, the method comprising: scanning the spinal cord or peripheral nerve location in the host needing treatment to determine the area of the injury; and three-dimensionally printing the implant to encompass the area of injury.

BRIEF DESCRIPTION OF THE DRAWINGS

FIGS. 1A-E depict a 3D printed implant mimicking spinal cord architecture. FIG. 1A depicts a 3D printer setup including a UV light source (365 nm wavelength), a computer for sliced image-flow generation and system synchronization, a digital micromirror device (DMD) for optical pattern generation, a set of projection optics, a stage for sample position control, and a CCD imaging system for on-line monitoring of the fabrication process. FIG. 1B depicts microscale continuous projection 3D printing (µCPP) layerless 3D printing which creates structures without discrete layers as often observed in inkjet 3D printers. FIG. 1C depicts heavy chain neurofilament (NF200) labeling of axons in intact T3 rat spinal cord. Rostral to the left, caudal to the right of image. Axons in the white matter (top of the panel) are highly organized into parallel arrays traveling from rostral to caudal, while axons in the gray matter (bottom of the panel) are not present in linear arrays. The disclosed implant mimics the linear organization of white matter. White line demarcates the interface between white and gray matter. FIG. 1D depicts projections of different axon tracts (fascicles) in the dorso-lateral quadrant of the T3 rat spinal cord. The rubro-rubrospinal tract (Ru), raphe-raphespinal tract (Ra), reticulo-reticulospinal tract (Ret), proprio-propriospinal tract (Pr), spinothalamic-spinothalamic tract (ST), and CST-corticospinal tract (C) are illustrated. The central butterfly-shaped portion is the core of the implant (analogous to the "grey matter" of the normal spinal cord) and the remainder of the illustration is the shell of the implant (analogous to the "white matter" of the normal spinal cord). FIG. 1E depicts guidance achieved in the rostro-caudal axis, thereby guiding regenerating axons (line) to their proper tract on the distant side of the lesion. Arrows point to the point of entrance and exit of regenerating axons in the implant showing the implant maintains the exact 3D coordinates throughout the lesion site, matching to the natural host architecture.

FIG. 2 depicts mechanical measurements of implant elastic modulus using dynamic mechanical analysis (DMA).

FIG. 3A illustrates a sagittal mid-cervical T1-weighted magnetic resonance (MR) image of human clinically complete (ASIA A) spinal cord injury. A sliver of spared host white matter is evident on the anterior aspect (right side) of the lesion (arrow). FIG. 3B illustrates a traced outline of the cystic lesion cavity from FIG. 3A. FIG. 3C illustrates a computer-aided design (CAD) 3D model of a implant to be 3D printed, corresponding to a precise lesion shape. FIG. 3D illustrates a printed implant. FIG. 3E illustrates a hypothetical fit of the printed 3D implant of FIG. 3D in a human contusion cavity.

FIG. 4 illustrates a cross-sectional image of an implant in a lesion site labeled for axons (neurofilament NF200) showing that overall implant structure remains intact four weeks after implantation (transverse section). The scale bar is 500 μm.

FIG. 5C depicts quantification of the reactive cell layer (RCL) thickness, ±S.E.M. *p<0.05 (Student's t-test).

FIGS. 6A-D depict 3D printed implants implanted into spinal cord injury sites four weeks after implantation. Depicted are a host glial scar revealed by glial fibrillary acidic protein (GFAP) immunoreactivity in animal with lesion only (no implant) (FIG. 6A), agarose scaffold in lesion site (FIG. 6B), or 3D printed implant in lesion site (FIG. 6C) (rostral to the left, caudal to the right). The scale bar for FIG. 6A and 6B is 250 μm and 100 μm for FIG. 6C. Note that a GFAP-labeled barrier is not present around a 3D printed PEGDA/GelMa implant; instead, glial fibers are arranged longitudinally into the channels where they can potentially support extending axons. FIG. 6D depicts quantification of GFAP intensity in host spinal cord surrounding lesion site, ±S.E.M. *p<0.05 (ANOVA with post-hoc Tukey's).

FIG. 9A is an electron micrograph image within a channel demonstrating axons (asterisks) that are associated with a neighboring ensheathing Schwann cell (Sc). The scale bar is 1 μm. FIG. 9B depicts a magnified channel from FIG. 9A showing S100-labeled Schwann cells ensheathing NF200-labeled axons (arrow). The scale bar is 5 μm. FIG. 9C is an electron micrograph of a channel demonstrating a myelinated axon in the implant with a Schwann cell (SC). The scale bar is 0.5 μm.

FIGS. 10A-H depict the 3-D printed implants disclosed herein and loaded with neural stem cells, four weeks after implantation into rats. FIG. 10A depicts channels that are filled with GFP-expressing neural stem cells (arrows) (horizontal section). The scale bar is 200 μm. FIG. 10B depicts a rostral entrance to channel that is penetrated by host NF200-labeled axons; host cells are distinguished from graft-derived axons by absence of GFP expression. The scale bar is 50 μm. FIG. 10C depicts implanted neural stem cells extend GFP-expressing axons that are linearized by the implant linear architecture. FIG. 10D depicts 5HT-labeled host serotonergic axons entering a stem cell-filled channel from rostral (left) aspect of a lesion and regenerating linearly in the channel (arrow). The scale bar is 100 μm. FIG. 10E depicts serotonergic axons regenerating linearly into an empty implant lacking stem cells, although the number of penetrating axons is reduced. The scale bar is 100 μm. FIG. 10F depicts 5HT-labeled host serotonergic axons regenerating to the caudal end of a implant containing stem cells, respecting the linear boundaries created by implant architecture. The scale bar is 50 μm. FIG. 10G depicts quantification of 5HT axons reaching the caudal part of the implant. *p<0.05 (ANOVA, +S.E.M.). FIG. 10H depicts 5HT-labeled motor axons exiting the caudal aspect of the channel to regenerate into the host spinal cord distal to the lesion (arrow). The line demarcates the exit from caudal channel to caudal spinal cord. The scale bar is 50 μm.

FIG. 12A depicts axons of varying diameters (asterisks) are present within channels and many axons are myelinated (M) Scale bar is 500 nm. FIG. 12B depicts oligodendrocytes sending multiple processes to myelinate and ensheath axons. Scale bar is 0.2 μm.

FIG. 14A depicts 5HT host axons regenerating into implant channels form appositional contacts (arrows) with dendrites (labeled with Map2) of implanted neural stem cells (GFP) four weeks after implantation. The scale bar is 10 μm. FIG. 14B depicts quantification of 5HT axons reaching the caudal end of the implant. *p<0.05 (ANOVA P<0.01, post-hoc Tukey's P<0.01 comparing both NSC-implant groups to either the NSC graft-only group and the empty implant group).

FIG. 15A-E depict anatomy 6 months post implant. FIG. 15A: Channels remain structurally intact and are filled with GFP-expressing neural stem cells. Horizontal section, rostral to left. FIG. 15B: Corticospinal axons anterogradely labeled with RFP enter the implant and extend linearly in a caudal direction, aligned by implant architecture. Horizontal section. FIG. 15C: Corticospinal axons (CST) axons converge on NeuN labeled neuron inside the channel, forming potential bouton-like contacts with the soma. FIG. 15D: GFP-immunoreactive axons extend out from the implant into host white and gray matter caudal to the lesion. Ventrolateral white matter, 2 mm caudal to the lesion. FIG. 15E: Neural Stem Cell (NSC)-derived GFP-labeled axons form potential bouton-like structures on gray matter NeuN-immunoreactive host neurons located 2 mm caudal to the lesion. FIG. 15F-G depict behavioral studies. FIG. 15F: Neural stem cell/implant treated animals exhibit significant functional recovery on the BBB locomotor scale five months post implant reflecting consistent movement of each of the three joints of both hind limbs (**p<0.05, *p<0.01). FIG. 15G: Schematic of electrophysiology study performed 6 months post implant. Transcranial electrical stimulation was applied to the motor cortex in the brain and Motor Evoked Potentials (MEPs) were recorded from hindlimbs.

FIG. 16D depicts that the mean MEP amplitude is significantly greater in animals implanted with neural stem cell-containing implants (p<0.01).

FIG. 18D depicts the thickness of RCL is significantly reduced in PEGDA-GelMa implants (p<0.05, ANOVA; post-hoc Tukey's comparing PEGDA group to agarose and HA scaffolds). Average±s.e.m. The scale bar is 250 μm.

FIGS. 20A-D depict regeneration of neurons, 4 weeks post implantation. FIGS. 20A-D depicts GFP-labeled implants from 4 different animals demonstrating complete and uniform fill of channels with rodent neural stem cells, which also occupy interfaces between implants and host (arrows). The scale bar is 0.5 mm.

FIG. 22 depicts stem cell differentiation marker distribution in graft cells inside the channels.

FIG. 23 depicts a serotonergic axon (arrow) is visible in a stem cell graft injected into the lesion site without an implant; the axon is vertically oriented and therefore misaligned in the rostral-to-cadual axis of the lesion site. The interrupted line demarcates graft-host interface. Rostral to the left, caudal (lesion site) to the right. The scale bar is 50 μm.

FIG. 24A-B depict channels lacking a stem cell fill (FIG. 24A) or stem cell grafts without an implant (FIG. 24B), contain substantially fewer 5HT-labeled axons at the caudal aspect of the implant. The scale bar is 50 μm.

DETAILED DESCRIPTION

Disclosed herein are implants and methods for rapid three-dimensional (3D) microscale printing of regeneration-promoting implants which biomimic the complex fascicular microscale architecture of the spinal cord or peripheral nerves. The implants, comprised of a polymer, can be rapidly printed and are scalable to clinically relevant spinal cord or peripheral nerve sizes and lesion geometries. Injured host axons regenerate into 3D biomimetic implants, synapse onto neural stem cells implanted into the device, and implanted neural stem cells in turn extend axons out of the implant and into the host spinal cord, or peripheral nerve, below the injury to restore synaptic transmission and significantly improve functional outcomes. New replacement electrophysiological relays across the injury site form that support significant functional motor improvement. Thus, complex 3D biomimetic implants offer a means of enhancing central nervous system regeneration through precision medicine.

Described herein are medical implants that assist in restoring bodily function. The function can be restored in a mammal that can include a human, a horse, a pig, a cow, a bull, a goat, a sheep, a dolphin, a dog, a cat, a camel, or the like. In one embodiment, the mammal is a human. In some embodiments herein, the mammal is referred to as a host.

These medical implants can be used in some embodiments to promote axonal regeneration after spinal cord or peripheral nerve injury.

In some embodiments, the medical implants comprise a three-dimensional implants and optionally stem cells. In some embodiments, the implants are produced by 3D printing. These implants can be custom designed to fit a particular patient's anatomy. The terms "scaffold" and "implant" are used interchangeable and refer to the 3D printed structure with or without stem cells.

While bioengineered scaffolds or implants support axon regeneration into spinal cord, or peripheral nerve, lesion sites, these technologies have been limited by foreign body responses at implantation sites, cumbersome production requirements, limitations in scaling to human-sized injuries and lack of biomimicry of the natural spinal cord or peripheral nerve. The implants and methods of using the implants described herein include structures which biomimic complex fascicular architecture of a spinal cord or peripheral nerve. The implants, which can be printed, can be simply and rapidly produced, reduce foreign body responses, and/or support linear, aligned host axonal regeneration across a lesion site. Moreover, neural stem cells can be loaded into the implants. The stem cells can support regenerating host axons as they cross the lesion site and bridge beyond, and facilitate functional regeneration in vivo.

Figure 1C:
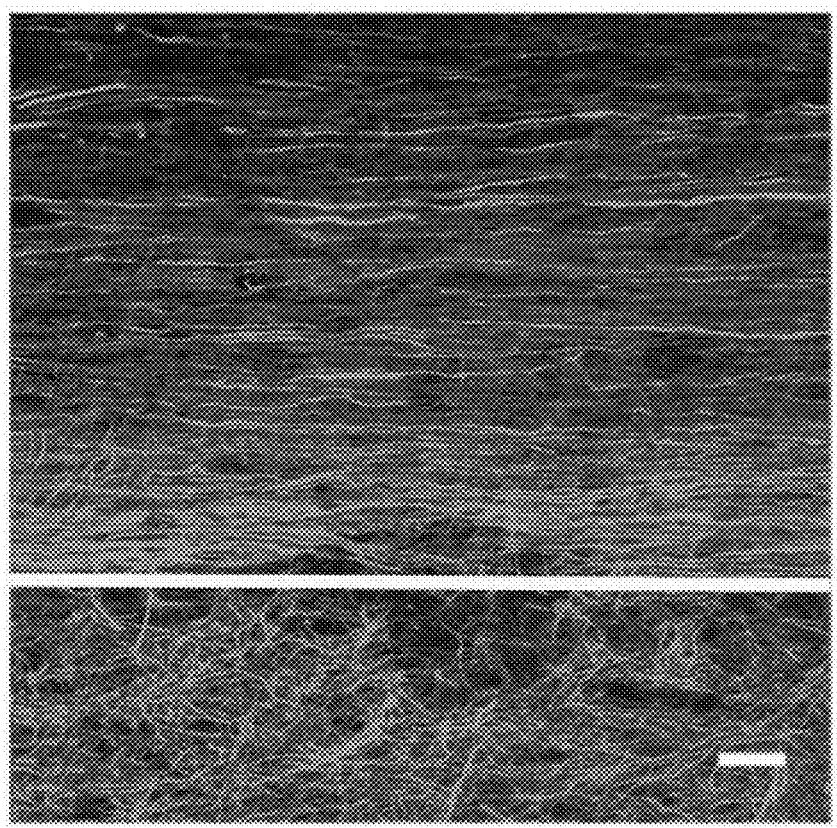
Figures 1E, 2:
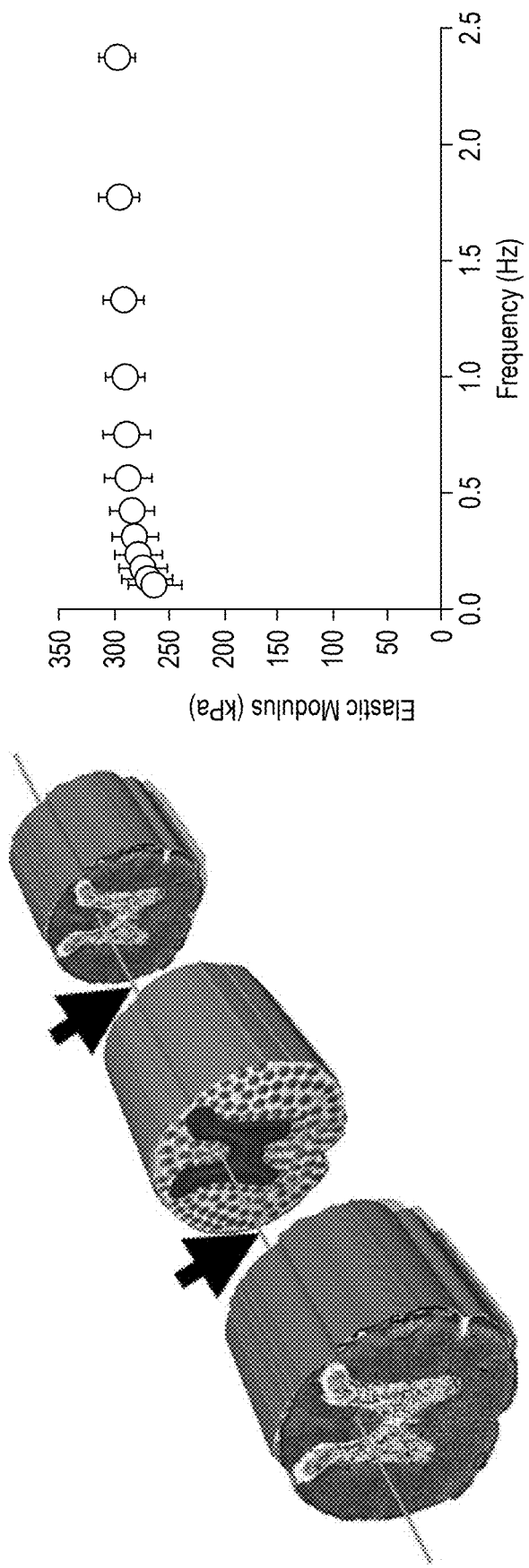
Figure 3E:
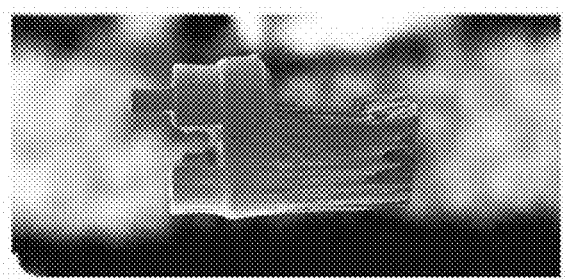
FIGS. 3A-E depict an exemplary spinal implant as disclosed herein.
Figure 3D:
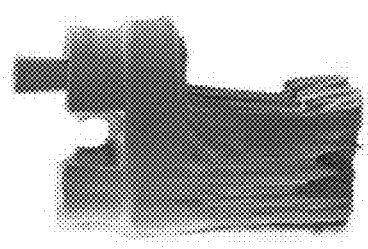
Figure 3C:
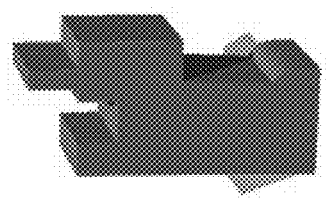
Figure 3B:
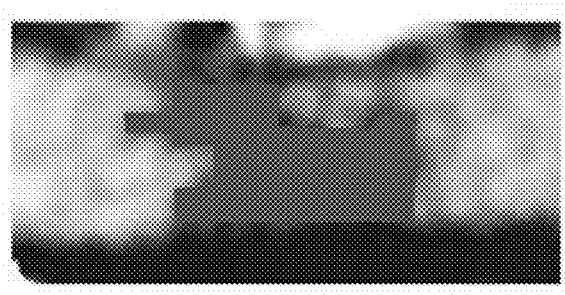
Figure 3A:
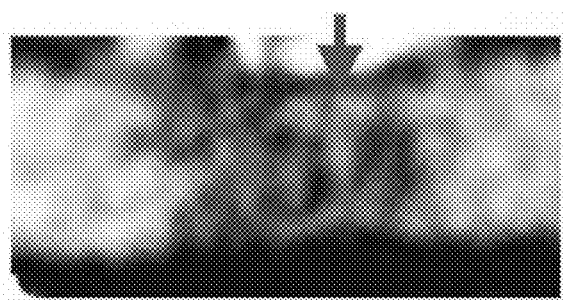

A spinal cord is used as a template to design a spinal cord implant (FIG. 1A). Microchannels are included to provide alignment of implant channels with host axonal tracts above and below the injury (FIG. 1D-E). The inner "gray matter" area of the spinal cord is normally free of axons projecting below the injury site, thus this component of the implant, the core, is designed as a solid region that enhances structural integrity of the implant (FIG. 1D). Use of agarose microchanneled implants demonstrated that 80% of host axons entering a lesion site could be guided by linear, or parallel, conduits to reach the opposite (caudal) end of the lesion. However, agarose elicited a foreign body response consisting of a collagen-based reactive cell layer that attenuated and trapped axons within the implant, preventing axon growth beyond the channels. Thus, disclosed herein are implants fabricated from a mix of degradable materials that reduce the reactive cell layer due to reduction in a foreign body response, allowing host axons to better penetrate and even traverse beyond the lesion.

The materials used to form the implants comprise biologically acceptable polymers. In some embodiments, the polymer can include polyethylene glycol based polymers such as, but not limited to polyethylene glycol diacrylate (PEGDA) and poly(ethyelene glycol) diacrylamide. In some embodiments, the polymer can include gelatin methacrylol (GelMA) hydrogels. In some embodiments, the polymers can include combinations of polyethylene glycol diacrylate, poly(ethyelene glycol) diacrylamide, and gelatin methacrylol. In some embodiments, the polymers can include combinations of polyethylene glycol diacrylate and gelatin methacrylol. In some embodiments, the polymers can include combinations of poly(ethyelene glycol) diacrylamide and gelatin methacrylol.

In some embodiments, the biocompatible material PEGDA is used as the implant material. PEGDA itself is non-adhesive for cells, therefore gelatin methacrylate (GelMa), a photopolymerizable denatured collagen that retains cell binding ligands and matrix metalloproteinase degradation sites, is included to support attachment of cells to implant walls and long-term cell viability. Various concentrations of each material and the crosslinking density of printed implants were tested until combinations were identified that mimic mechanical properties of native spinal cord, or peripheral nerve, tissue, because a mismatch of mechanical properties between an implant and host could lead to compression or laceration at spinal cord, or peripheral nerce interfaces, causing a failure in integration.

An advantage of 3D bioprinting is an ability to rapidly print implants of different sizes and irregular shapes to conform to individual patient lesion sites that can be identified on magnetic resonance imaging (MRI). An implant formed of PEGDA/GelMa was printed to conform to the precise shape of a human spinal cord lesion cavity according to MRI, as shown in FIG. 3A-E. Implants that conform to the morphology of even complex human injury cavities have been printed.

The implants disclosed herein comprises a core and a shell. The core is analogous to the "grey matter" portion of the normal spinal cord or peripheral nerve and the shell is analogous to the "white matter" portion of the normal spinal cord or peripheral nerve.

The implants can include one or more channels. In some embodiments, the channels are in the shell. In some embodiments, the one or more channels extend from a first surface to a second surface. In some embodiments, the first surface is a top surface and the second surface is a bottom surface. In some embodiments, the first surface is a bottom surface and the second surface is a top surface. In some embodiments, the first surface is a first side surface and the second surface is a second side surface. In some embodiments, the first surface is a top surface and the second surface is a side surface. In some embodiments, the first surface is a bottom surface and the second surface is a side surface.

The channels can have a cross-sectional shape that is conducive to tissue ingrowth. In some embodiments, the cross-sectional shape can be square, triangle, pentagon, hexagon, heptagon, octagon, rectangle, trapezoid, ellipse, torx, star shaped with any number of arms, clover shaped, leaf shaped with any number of arms, other curvilinear or rectilinear shape, or the like, or a combination thereof. In some embodiments, a group or cluster of channels can have a honeycomb configuration.

In some embodiments, two or more different channel cross sections can be used in a single implant. In some embodiment, some channels are rectangular in cross-section and some are hexagonal (making a honeycomb structure). Any combination that achieves a therapeutic use can be used.

In some embodiments, the implants can be loaded with at least one type of stem cell. In some embodiments, the at least one type of stem cell is a neural stem cell. The neural stem cell is an embryonic stem cell, a iPSC derived stem cell, a differentiated stem cell, directly differentiated neural stem cells (e.g., differentiation from skin to neurons without going through a stem cell state), a GFP-expressing neural stem cell, or a combination thereof. In other embodiments, the at least one type of stem cell is a mesenchymal stem cell. The stem cell can be engineered to express BDNF, NT3, GDNF, or a combination thereof.

The implants can be formed at virtually any length. In some embodiments, implants can have lengths of about 1 mm, about 2 mm, about 3 mm, about 4 mm, about 5 mm, about 6 mm, about 7 mm, about 8 mm, about 9 mm, about 10 mm, about 20 mm, about 30 mm, about 40 mm, about 50 mm, between about 2 mm and about 4 mm, between about 2 mm and about 10 mm, or between about 2 mm and about 20 mm.

In some embodiments, the implants can be formed in shapes and with structures that mimic spinal cord architecture. These structures can include, but are not limited to, axon tracks and channels. The axon tracks can include the rubro-rubrospinal tract, raphe-raphespinal tract, reticulo-reticulospinal tract, proprio-propriospinal tract, spinotha-lamic-spinothalamic tract, and CST-corticospinal tract.

In some embodiments, the implants can include entrances and exits to axons in the implants, referred to herein as "channels", that maintain 3D coordinates throughout the lesion site, matching natural host architecture.

In some embodiments, the implants can have an elastic modulus of greater than about 250 kPa, greater than about 200 kPa, greater than about 300 kPa, between about 250 kPa and about 300 kPa, or between about 200 kPa and about 300 kPa.

In some embodiments, the implants are substantially biostable. Substantially biostable means that the implants are more than 80%, 90%, 95%, 99%, or full intact after 3 months, after 4 months, after 5 months, after 6 months, after 1 year, or after five years after implantation.

In some embodiments, the implants can resist collagen deposition on their surfaces. In some embodiments, the herein described implants can reduce collagen deposition when compared to an implant formed of another polymer or metal material by greater than about 50%, greater than about 60%, greater than about 70%, greater than about 80%, greater than about 90%, or greater than about 95%.

In some embodiments, the implants can resist reactive cell deposition (or reduce the size of the reactive cell layer) at the site of implantation. In some embodiments, the herein described implants can reduce the size of the reactive cell layer when compared to an implant formed of another polymer or metal material by greater than about 20%, greater than about 30%, greater than about 40%, greater than about 50%, or greater than about 60%. In some embodiments, the herein described implants can reduce the size of the reactive cell layer when compared to an implant formed of agarose by greater than about 20%, greater than about 30%, greater than about 40%, greater than about 50%, or greater than about 60%.

In some embodiments, the implants can attract a minimal reactive cell layer after implantation that has a thickness of less than about 400 μm, less than about 350 μm, less than about 300 μm, less than about 250 μm, or between about 400 μm and about 200 μm.

In some embodiments, the implants can reduce glial scar formation at the site of implantation when compared to an implant formed of another polymer or metal material by greater than about 50%, greater than about 60%, greater than about 70%, greater than about 80%, or greater than about 90%. Glial scar formation (gliosis) is a reactive cellular process involving astrogliosis that occurs after injury to the central nervous system. In some embodiments, the implants can reduce glial scar formation at the site of implantation when compared to an implant formed of agarose by greater than about 50%, greater than about 60%, greater than about 70%, greater than about 80%, or greater than about 90%.

In some embodiments, the implants can reduce glial scar formation at the site of implantation when compared to an untreated lesion by greater than about 20%, greater than about 30%, greater than about 40%, greater than about 50%, or greater than about 60%.

When compared to an agarose implant, the present implants can result in glial fibers that are arranged longitudinally into the channels where they can potentially support extending axons.

The herein described implants can be well-vascularized thereby allowing blood vessels to infiltrate the implant.

Further, the implants can allow axons to penetrate the implant material. This penetration is in contrast to other implants, such as agarose-based implants, where axons fail to cross astrocyte scars that occur around those implants. Axons that penetrate the herein described implants can associate with neighboring ensheathing Schwann cells.

In some embodiments, when the implants are loaded with at least one type of stem cell, host axons can enter a stem cell-filled channel and regenerate linearly, or parallely, in the channel. In other embodiments, host serotonergic axons can enter a stem cell-filled channel from a rostral aspect of a lesion and regenerate linearly, or parallely, in the channel. In some embodiments, serotonergic axons can enter an implant and regenerate linearly, or parallely, in a channel even when stem cells are not present. However, this regeneration can be reduced by about 10% to about 20%, about 20% to about 30%, about 30% to about 40%, or about 40% to about 50% compared to stem cell-containing implants.

In some embodiments, the regenerating host axons can reach the caudal part of the implant. In some embodiments, when loaded with at least one type of stem cell, the implants cause an increase in axons reaching the caudal part of the implant by at least about 50%, at least about 80%, at least about 100%, or at least about 120% when compared to an implant without stem cells.

In some embodiments, the implants can allow motor axons to exit a caudal aspect of a channel to regenerate into the host spinal cord, or peripheral nerve, distal to the lesion. In other embodiments, motor axons can remain detectable up to about 3.5 mm, up to about 2.5 mm, or up to about 4.5 mm beyond the lesion.

In some embodiments, the channels in the herein described implants can accommodate or solicit axons of varying diameters. Further, the axons that regenerate within the channels can be myelinated. In some embodiments, when axons form in the channels, synapses can form between axons within channels and the dendrites of implanted neural stem cells. The synapses can be asymmetric and/or pre-synaptic boutons containing rounded vesicles. In some embodiments, at least a portion of the formed synapses can be excitatory.

In some embodiments, host axons can regenerate into channels and form appositional contacts with dendrites of implanted neural stem cells.

In some embodiments, the herein described implants can provide at least partial recovery of motor evoked potential (MEP) responses. Motor evoked potentials are recorded from muscles following direct stimulation of the spinal cord, either magnetic or electrical. In some embodiments, these MEP responses can be in the arms and/or legs including fingers and toes. A stem cell-loaded implant can increase MEP responses when compared to an empty implant by about 4 times to about 10 times, about 3 times to about 10 times, about 4 times to about 8 times, or about 3 times to about 8 times.

In some embodiments, the herein described implants can provide at least partial functional improvement of post-injury motor behavior. Post-injury motor behavior in rodents is measured via the Basso, Beattie and Bresnahan (BBB) motor scale. The scale (0-21) represents sequential recovery stages and categorizes combinations of joint movement, hindlimb movements, stepping, forelimb and hindlimb coordination, trunk position and stability, paw placement, and tail position.

In some embodiments, after implantation, implant channels can be uniformly filled with stem cells. In some embodiments, after implantation, channels can be uniformly filled with neural stem cells. In some embodiments, the stem cells can occupy interfaces between the implant and the host. In some embodiments, stem cell-derived cells in the channels can express a neuronal marker, such as, but not limited to, Hu or NeuN. In other embodiments, the stem cell-derived cells in the channels can express an oligodendrocyte marker, such as but not limited to, Olig2 or an astrocyte marker such as, but not limited to, GFAP. In some embodiments, the cells can express two or more of the above.

Surprisingly, in some embodiments, no serotonergic neuronal cell bodies exist in the spinal cord-derived neural stem cell grafts. In some embodiments, substantially no serotonergic neuronal cell bodies exist in the spinal cord-derived neural stem cell grafts.

In some embodiments, hosts implanted with the herein described implants loaded with at least one type of stem cell can exhibit shorter MEP latency relative to hosts implanted with empty implants. In some embodiments, hosts implanted with the herein described implants loaded with at least one type of stem cell can exhibit MEP latency that closely resembles latency observed in intact hosts. In some embodiments, MEP latency can be between about 9 ms and about 12 ms, between about 8 ms and about 10 ms, between about 8 ms and about 12 ms, between about 9 ms and about 10 ms, or between about 7 ms and about 13 ms.

As discussed, in some embodiments, the implants described herein are printed. Bioprinting functional tissue, generally, faces many challenges, among which are a lack of appropriate biofabrication techniques to build complex 3D microarchitectures essential for guiding cell growth and promoting tissue maturation. Common inkjet or extrusion-based bioprinting approaches use nozzles to deposit materials allowing printing of simple 2D structures such as skin, cartilage and simple 3D structures such as blood vessels, aortic valves, and tracheas.

In some embodiments, an implant as described herein can be fabricated using microscale continuous projection 3D printing (μCPP). Microscale continuous projection printing can fabricate complex 3D architectures with a variety of biomaterials and cells. Such printing can be accomplished without scanning in both X and Y directions (in contrast to nozzle-based approaches). Thus, 3D objects can be fabricated in one continuous print in the Z direction. In some embodiments, only seconds may be required to print an entire implant. In some embodiments, an implant can be printed in about 1 second, about 2 seconds, less than about 2 seconds, less than about 3 seconds, less than about 4 seconds, less than about 5 seconds, less than about 10 seconds, less than about 20 seconds, or less than about 30 seconds. In one embodiment, about only 1.6 seconds is required to print an entire 2 mm implant. This print rate represents a rate about 1,000 times faster than traditional nozzle printers.

Using focused light for polymerization generates printing resolution of 1 μm, a 50-fold improvement over nozzle-based inkjet printers. In inkjet or extrusion-based approaches, mechanical integrity may be compromised by artificial interfaces between the drops or lines and can cause mechanical failure during or after in vivo application. By providing layerless resolution in the Z direction, the structures may not exhibit these planar artifacts (interfaces) induced by a movement of a linear stage to a new position. Thus, μCPP as described herein can improve mechanical integrity of 3D printed implants and offer rapid fabrication of complex 3D biomimetic structures at microscale resolution.

In some embodiments, the implant is printed in a single portion for implantation at a site of spinal cord transection or a peripheral nerve injury. In some embodiments, the implant is printed in two or more portions whereby a damaged, but not transected, spinal cord, or peripheral nerve, can be treated with an implant disclosed herein. If the spinal cord injury (SCI), or peripheral nerve injury, is not a transection, the one or more portions of the implant can be implanted surrounding the surviving tissue and the portions adhered to each other using a biologically acceptable adhesive. Thus, any surviving tissue can be maintained and regeneration of the host spinal cord, or peripheral nerve, encouraged at the injury site.

An implant is customized for each patient. Upon imaging of a patient spinal cord, or peripheral nerve, injury a 3D model is created using CAD software. This model is then used to print a patient specific implant that fit and fill the lesion. Thus, sometimes it is not necessary to print the whole implant as designed in if FIG. 1D. If the injury is not as big as the whole spinal cord (partial lesion) than the model would be smaller than that shown in FIG. 1D. The physician will have the final decision on which part, or all, or the lesion site might be filled with an implant. For example, the physician might decide to print only the channels part (without the butterfly shape).

In other embodiments, a 3D printed biomimetic implant is printed based on a spinal cord, or peripheral nerve, injury and only a portion of the printed implant is implanted at the injury site. In some embodiments, only the honeycomb portion is implanted.

The implant described herein can exhibit in vivo stability and support axon regeneration and remyelination across sites of severe (complete) SCI. More than 500,000 people in the United States suffer from SCI, with resulting substantial psychological and economic costs to both patients and caregivers. Three-dimensional printing using the herein described devices and methods can allow fabrication of personalized implants that "fit" the precise anatomy of an individual's injury to stimulate, guide, and align axon regeneration. Moreover, the implants can be loaded with neural stem cells to produce implants that further support neural repair or remyelination.

In some embodiments, host motor axons can regenerate and bridge beyond a complete spinal cord, or peripheral nerve, lesion site into the distal spinal cord, or peripheral nerve, through a biomimetic implant.

In other embodiments, the present implants and treatment methods can support regaining of function in the most challenging model of SCI, complete spinal cord transection.

In some embodiments, the convergence of rapid 3D printing and stem cell biology, the present implants can offer spinal cord, or peripheral nerve, treatment by providing patient-specific regenerative therapy.

In some embodiments, the present implants can promote axonal regeneration after spinal cord or peripheral nerve injury.

In some embodiments, the present implants can provide regeneration or remyelination of greater than hundreds of injured host axons over distances from 1-20 millimeters or more. In some embodiments, the present implants can provide regeneration or remyelination of greater than thousands of injured host axons over distances from 1-20 millimeters or more. In some embodiments, the present implants can provide regeneration or remyelination of host axons over distances from 1-20 mm, from 1-10 mm, from 1-5 mm, from 1-4 mm, from 1-3 mm, from 1-2 mm, from 2-4 mm, from 3-4 mm, from 2-5 mm, or from 3-5 mm. In some embodiments, the present implants can support axons that can extend for distances greater than about 50 mm, greater than about 100 mm, greater than about 150 mm, greater than about 200 mm, or more.

In some embodiments, the present implants can provide hosts with functional improvement even after complete spinal cord, or peripheral nerve, transection. In some embodiments, the present implants can provide functional benefits to hosts following stem cell implantation that result in "splicing" the injured circuit, wherein host axons penetrate and synapse with neurons in the graft, and graft-derived axons in turn extend out from the lesion site and synapse with host intraspinal or peripheral neurons caudal to the injury.

In some embodiments, the present implants can optimize the functional usefulness of axons emerging from neural stem cell implants in lesion sites. In some embodiments, the present implants can align spliced circuits with their correct caudal white matter projections.

In some embodiments, the present implants can provide "custom fit" implants for individual patient lesions.

Methods of making the herein described implants are also described. The methods can include the steps of scanning a region needing treatment and printing an implant as described herein. The printing can be by 3D printing.

Further, described are methods of treating conditions using the herein described implants. Conditions can include, but are not limited to a neurological injury, spinal cord injury, motor complete spinal cord injury, motor incomplete spinal cord injury, a peripheral nerve injury, bowel dysfunction, incontinence, impotence, other sexual dysfunction, pain, numbness, neuropathy, unregulated body temperature, and the like, or combinations thereof. Certain of these conditions are the sequelae of the spinal cord injury and therefore treating the injury site, and restoration of function at the injury site, will treat one or more of the sequelae.

In one embodiment, methods for treating a neurological injury are described. Methods for treating a neurological injury can include scanning a region needing treatment, printing an implant as described herein, implanting the implant into a location within the region, and treating the neurological injury.

In one embodiment, methods for treating a spinal cord injury are described. Methods for treating a spinal cord injury can include scanning a region needing treatment, printing an implant as described herein, implanting the implant into a location within the region, and treating the spinal cord injury.

In some embodiments, methods for treating a motor complete spinal cord injury are described. Methods for treating a motor complete spinal cord injury can include scanning a region of the spinal cord needing treatment, printing an implant as described herein, implanting the implant into a location within the region, and treating the motor complete spinal cord injury.

In some embodiments, methods for treating paralysis are described. Methods for treating paralysis can include scanning a region of the spinal cord needing treatment, printing an implant as described herein, implanting the implant into a location within the region, and treating the paralysis.

In some embodiments, methods for treating bowel dysfunction resulting from a spinal cord injury are described. Methods for treating bowel dysfunction resulting from a spinal cord injury can include scanning a region of the spinal cord needing treatment, printing an implant as described herein, implanting the implant into a location within the region, and treating the bowel dysfunction resulting from a spinal cord injury.

In some embodiments, methods for treating impotence resulting from a spinal cord injury are described. Methods for treating impotence resulting from a spinal cord injury can include scanning a region of the spinal cord needing treatment, printing an implant as described herein, implanting the implant into a location within the region, and treating the impotence resulting from a spinal cord injury.

In some embodiments, methods for treating pain are described. Methods for treating pain can include scanning a region of the spinal cord needing treatment, printing an implant as described herein, implanting the implant into a location within the region, and treating the pain.

In some embodiments, the methods for treating a peripheral nerve injury are described. Methods for treating a complete or partial peripheral nerve injury can include scanning a region of the peripheral nerve site needing treatment, printing an implant as described herein, implanting the implant into a location within the region, and treating the peripheral nerve injury.

In some embodiments, the location can be a spinal cord lesion.

In some embodiments, the location can be a peripheral nerve lesion.

In some embodiments, the methods of treatment can further include subjecting the individual to other therapeutic modalities. These treatment modalities can include training devices or systems configured to physically train the subject and thereby provide additional neurological signals in the portion of the subject's body impaired by the injury. Training devices can use robotics, exoskeletons, treadmills, canes, walkers, crutches, body weight support systems, physical therapy, or a combination thereof to aid in training.

In some embodiments, the methods of treatment can further include growing axons through the implant channels.

Kits are also described. Kits can include an implant and instructions for use in a unifying container.

Some kits can include a scan of a region needing treatment and instructions for use in a unifying container.

Other kits can include a scan of a region needing treatment, the polymers needed to print an implant, and instructions for use in a unifying container.

Other kits can include a scan of a region needing treatment, PEGDA and GelMa to print an implant, and instructions for use in a unifying container.

EXAMPLE 1

Rat spinal cord was used as a template to design a spinal cord implant.

Implant materials used in this Example: PEGDA (Mn=700 Da) was purchased from Sigma-Aldrich (USA). Gelatin methacrylate (GelMa) was synthesized as described in previous reports (Soman, P. et al., Biotechnol Bioeng 110:3038-3047, 2013). Photoinitiator lithium phenyl-2,4,6-trimethylbenzoylphosphinate (LAP) was synthesized as previously reported (Fairbanks, B. D. et al., Biomaterials 30:6702-6707, 2009). The matrix material used for printing the implants was made by mixing 7.5% (w/v) GelMa, 25% (v/v) PEGDA and 0.225% (w/v) LAP in Dulbecco's phosphate-buffered saline (DPBS).

Implant 3D printing used in this Example: The 3D bioprinter described herein (µCPP) includes the following six components as shown in FIG. 1A: (1) UV LED light source (365 nm) for photopolymerization; (2) a digital micromirror array device (DMD) chip (Texas Instruments) consisting of 1920×1080 micromirrors for optical pattern generation; (3) projection optics for imaging the optical pattern on the DMD chip to the fabrication plane on the stage; (4) an automatic stage holding the monomer solution for fabrication; (5) a digital camera for real-time monitoring and imaging of the fabrication process; and (6) a computer coordinating the UV light source, the DMD chip, the stage and the camera for the 3D printing process.

Rat spinal cord implant printing used in this Example: Digital images of the core (representing the gray matter of the spinal cord) and the shell (representing the white matter of the spinal cord) were generated by processing the cross-section image of a spinal cord, which were later imported into the DMD chip to control the micromirrors during the printing process. Channels (200 µm in diameter) were incorporated in the shell to provide linear, or parallel, guidance for the axonal regeneration. The core was designed as a solid block of GelMa, 25% (v/v) PEGDA and 0.225% (w/v) LAP to enhance the mechanical strength of the printed implant. The monomer solution of the matrix material was loaded into a reservoir with 2 mm PDMS spacer to control the z-axis height of the printed implants. A continuous printing process was initiated using in-house developed software for controlling the 3D printer. The implant was printed in two steps, 0.8 second long each, one for the shell image and the next for the core image. The printed implant was then removed from the reservoir and rinsed three times with sterile DPBS and antibiotics (1% Pen Strep).

Human spinal cord implant printing used in this Example: A cervical MRI scan was used to model a typical chronic spinal cord injury. The lesion was traced and a 3D spinal cord Computer-Aided Design (CAD) model was used to match the human injury dimensions. The 3D model was then sliced into a series of digital masks along the longitudinal direction of the spinal cord, which were imported into the DMD chip sequentially. By dynamically changing the digital mask with the movement of the stage, the patient-specific spinal cord implant was using methods described above.

Fabrication of templated agarose scaffolds used in this Example: Multi-component fiber bundle (MCFB) templates were fabricated from 200 µm diameter polystyrene fibers (Paradigm Optics, Vancouver, WA) arranged in a hexagonal close-packed array separated by a continuous matrix of poly(methyl methacrylate) (PMMA). They were arranged with 66 µm interval spacing in a honeycomb array to generate final implants with wall sizes of 66 µm and channel diameters of 200 µm. Bundles were simultaneously extruded and fused such that polystyrene fibers were oriented parallel to the longitudinal axis of the bundles. The multi-component fiber bundle templates were trimmed to a length of 2 mm and a cross-sectional width and depth of 1.5 mm. Polystyrene end caps 1.5 mm in length were bonded to fiber bundle terminals using cyclohexane to anchor polystyrene fibers and form an external, rigid multi-component fiber bundle template. Six such multi-component fiber bundle units were then aligned in-series with two polystyrene side caps agglutinating into a linear template array. The poly(methyl methacrylate) matrix was then selectively removed by mmersion in 99.7% propylene carbonate (Sigma-Aldrich) three times, followed by 95% ethanol rinse and distilled water rinse. Ultrapure agarose (30 mg/ml, Sigma-Aldrich) was dissolved in distilled water at 100° C. and then cooled to 65° C. Multi-component fiber bundle templates were submerged into the agarose solution and centrifuged (300 rpm for 30 s) to permeate agarose through the packed polystyrene fiber array. The agarose cast was then allowed to gel at room temperature, trimmed, and immersed in 99% tetrahydrofuran (Sigma-Aldrich) at room temperature for 24 h. This was repeated twice to remove the polystyrene mold, resulting in individual free-floating agarose scaffolds. The scaffolds were collected and washed sequentially in acetone, 95% ethanol, and three cycles of sterile water. They were stored in sterile water at room temperature until use.

Preparation of E14 neural stem cells used in this Example: Briefly, spinal cords from GFP-expressing E14 F344 embryos were dissected and the meninges removed. The tissue was trypsinized for 15 minutes followed by centrifugation at 2,500 rpm at room temperature. Tissue was resuspended in NeuroBasal medium (Gibco) containing 2% B27 (Gibco), and the spinal cord tissue was gently triturated using progressively smaller fire-polished Pasteur pipets. Cells were then centrifuged at 2,500 rpm for 2 min, resuspended in NeuroBasal medium containing B27, and filtered using a 40 µm cell filter strainer.

Surgical procedures used in this Example: NIH guidelines for laboratory animal care and safety were strictly followed. Implants implanted into a complete transection at T3 spinal cord level was performed. Briefly, animals were deeply anesthetized, a T3 laminectomy was performed followed by a transection of the spinal cord using a combination of microscissors and microaspiration. A block of 1.8 mm was removed and a 2 mm long implant was implanted, thus the implant was retained securely between the transected segments of the spinal cord. Group 1 (n=14) received empty agarose scaffolds, group 2 (n=14) received empty 3D printed implants, group 3 (n=14) received 3D printed implants loaded with E14 neural stem cells suspended in a fibrin matrix containing a four-component growth factor cocktail: BDNF 50 ng/µL (Peprotech) to support neural stem cells survival, VEGF 10 ng/µL (Peprotech) and bFGF 10 ng/µL (Peprotech) to promote angiogenesis, and MDL28170 50 µM (Sigma), a calpain inhibitor for neuroprotection. Group 4 (n=8) had sham surgery where an injury was performed but no implant was implanted. Group 5 (n=8) received implants of rat E14-spinal cord-derived multipotent neural progenitor cells, as previously described (Lu, P. et al. Cell 150:1264-1273, 2012. Cells were suspended in the same fibrinogen/thrombin matrix with growth factor cocktail described above. Following the implant, the dorsal muscles and skin were sutured and antibiotics and analgesics were administered.

Microchannels (200 µm diameter) were designed to guide and align axons from their point of transection above the injury to their correct point of re-entry into the intact spinal cord below the injury (FIG. 1A-E). The inner core area is normally free of axons projecting below the injury site. Thus, this component of the implant was designed as a solid region that enhanced structural support of the implant.

Previous work with agarose microchanneled implants showed that 80% of axons entering the lesion site were guided by the implant and bridged to the opposite side of the lesion. However, agarose elicits a foreign body response consisting of a collagen-based reactive cell layer that attenuates and traps axons within the implant, preventing axon egress from channels. Thus, implants were fabricated from a degradable material that can reduce the reactive cell layer due to reduction in a foreign body response, allowing host axons to better penetrate and traverse the lesion. A combination of two biocompatible materials was used, polyethylene glycol diacrylate (PEGDA) and gelatin methacrylate (GelMa), as the implant material. PEGDA is non-adhesive for cells, therefore GelMa was added which is a photopolymerizable denatured collagen that retains cell-binding ligands and matrix metalloproteinase (MMP) degradation sites, potentially enhancing long-term cell viability. The concentrations of each material and the crosslinking density of printed implants can be designed to mimic the mechanical properties of the native spinal cord tissue, since a mismatch of mechanical properties between an implant and host could lead to compression or laceration at spinal cord interfaces, causing a failure in integration.

Dynamic Mechanical Analysis (DMA) was used to measure the elastic modulus of the 3D printed PEGDA/GelMa implants. The elastic modulus of the bioprinted implants used for implantation was within a range of 260 kPa-300 kPa (FIG. 2), in accordance with the native spinal cord elastic modulus of 200-600 kPa.

Immunolabeling was performed. Spinal cords were sectioned on a cryostat set at 20 µm intervals and processed for: 1) GFP labeling, to assess grafted cell survival and differentiation and axon extension (GFP rabbit polyclonal, Invitrogen, dilution of 1:500); 2) neural cell markers, including Hu for young neurons (Human polyclonal, dilution of 1:500), NeuN for mature neuronal nuclei (mouse monoclonal, Abcam, dilution of 1:500), MAP-2 for mature neurons (mouse monoclonal, BD Biosciences, dilution of 1:500), neurofilament 200 to label axons (mouse monoclonal, Millipore, dilution of 1:500), serotonin for mature neurons and axons (5HT, goat polyclonal, ImmunoStar, dilution of 1:500), glial fibrillary acidic protein for astrocytes (GFAP, chicken polyclonal, Millipore, dilution of 1:500), Olig2 for oligodendrocytes (Olig 2, mouse monoclonal, IBL, dilution of 1:200). 3) S100 to label Schwann cells (rabbit polyclonal, Dako, dilution of 1:500). 4) Collagen type IV (rabbit polyclonal, Biogenex, dilution of 1:500). Sections were incubated overnight at room temperature for primary antibodies, followed by incubation in Alexa 488-, 594- or 647- conjugated goat or donkey secondary antibodies (1:250, Invitrogen) for 3 hours at room temperature. Thickness of the reactive cell layer was measured in Nissl stained sections under 200× total magnification (eight sections per animal were quantified, with results expressed as mean±SEM). GFAP immunoreactivity was quantified as the mean gray value per Pixel measured at the host spinal cord—implant interface, on GFAP immunolabeled sections (eight sections per animal were quantified, with results expressed as mean±SEM). 5HT motor axons quantification was done using 200× magnified images of the 400µm portion of the caudal part of the channels (axons were counted manually and 8 sections per animal were quantified). Stem cell differentiation inside the channels was quantified using the above-mentioned antibodies. Each slide was counter-labeled with DAPI and GFP and cells were counted manually. Each cell type number was normalized to the total DAPI/GFP labeled nuclei in the channels (eight sections per animal were quantified. Quantification was done using ImageJ).

Statistical Analysis—Two-group comparisons were tested by two-tailed Student's t-test (JMP software) at a designated significance level of P<0.05. Multiple group comparisons were tested by one-tail ANOVA (JMP software) at a designated significance level of P<0.05, followed by post-hoc analysis using Tukey's test.

Electron Microscopy—Detailed analysis of synapse formation and myelination of axons was performed using electron microscopy as follows: subjects were perfused with 4% paraformaldehyde and 0.25% glutaraldehyde, spinal cords were post-fixed with 1% osmium tetroxide, dehydrated, and embedded in durcupan resin. Semi-thin sections of 0.5 µm were stained with toluidine blue for general morphology. Then, 60 nm sections were sectioned using ultramicrotome and visualized using FEI 200KV Sphera microscope at the UCSD CryoElectron Microscopy Core Facility.

Scanning Electron Microscopy imaging—Scanning electron microscopy (SEM, Zeiss Sigma 500) was used to image the patient-specific spinal cord implant. The implants were dehydrated in a series of ethanol baths and dried with a supercritical point dryer (Tousimis AutoSamdri 815A) then sputter-coated with iridium using Emitech K575X for 7 seconds at a deposition current of 85 mA. After sputter-coating, the implants were imaged using the Zeiss Sigma 500 SEM at 5 kV.

Functional Analysis—The BBB open field 21-point locomotion rating scale was assessed weekly by two independent observers blinded to group identity.

Electrophysiology—MEPs in the hind limbs were measured. Briefly, animals were anesthetized using propofol (100 mg/kg, PropoFlo Abbot). Transcranial electrical (pulse duration of 1 ms at 9 mV using a DS3 constant current isolated stimulator (Digitimer, Welwyn Garden City, UK)) using two percutaneously placed 30 G stainless steel stimulation electrodes. MEPs were recorded by ring electrodes placed on both hind limbs until three to five highest (stable) recorded potentials were similar. MEPs were recorded at week 26 post implant.

Figure 17B:
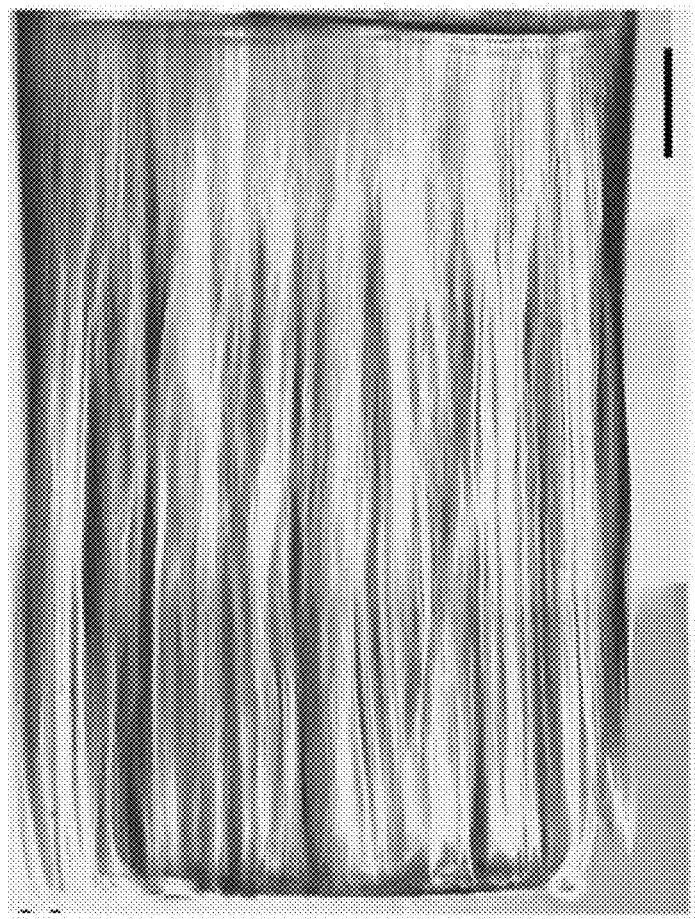
FIGS. 17A-B depict longitudinal images of printed implants in different lengths, (FIG. 17A) 2 mm and (FIG. 17B) 4 mm. The scale bar is 0.5 mm.
Figure 17A:
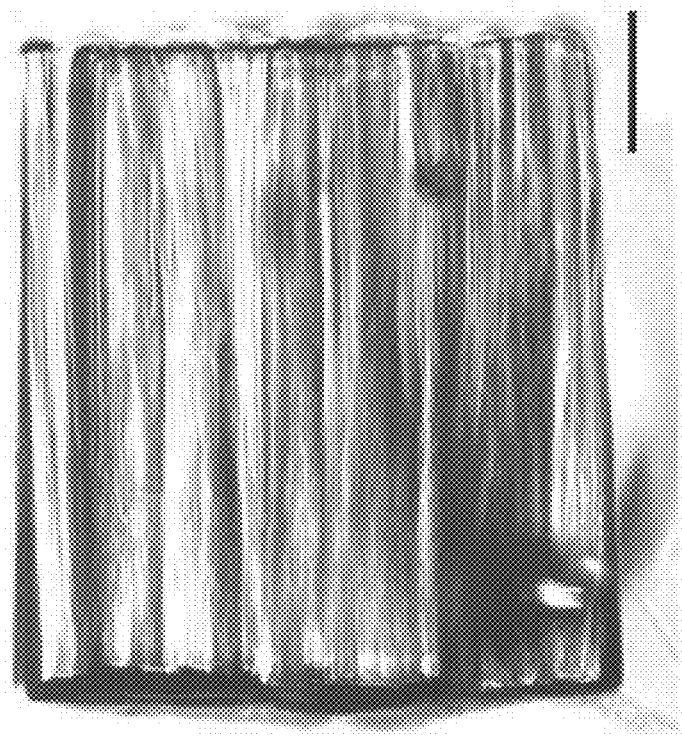
Figures 18A, 18B:
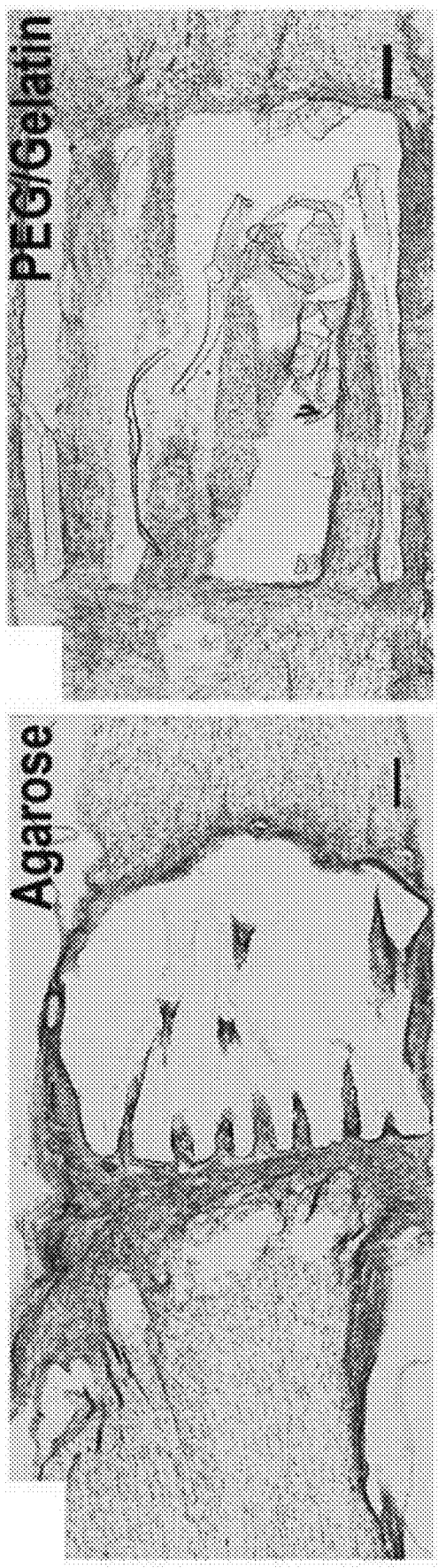
FIGS. 18A-D depict Nissl stains of agarose (FIG. 18A), PEGDA/GelMa (FIG. 18B), and hyaluronic acid implants (FIG. 18C) showing persistence of implant architecture in agarose and PEGDA at 4 weeks, and degradation of a hyaluronic acid scaffold.
Figure 18D:
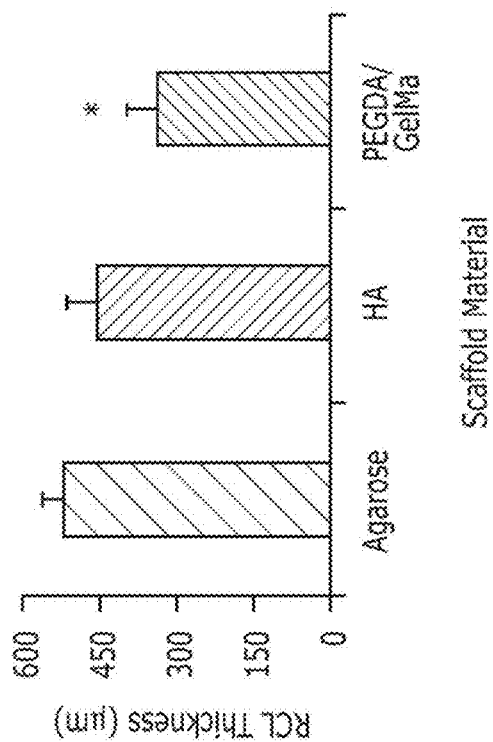
Figure 18C:
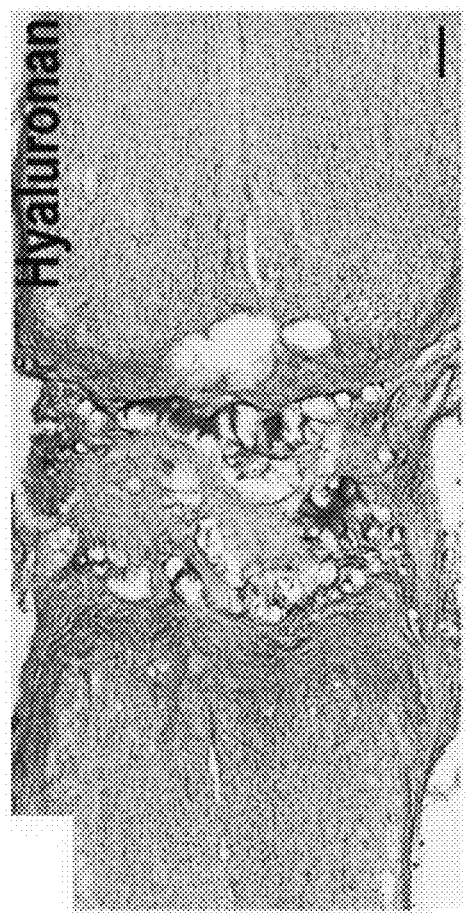

In some embodiments, an advantage of 3D bioprinting is the ability to rapidly print implants of different sizes (FIG. 17A-B) and unusual shapes to conform to individual patient lesion sites, as identified pre-operatively on MRI scans. An implant was printed to conform to the concise shape and size of a patient chronic lesion cavity, shown in FIG. 3A-E.

Bioprinted implants were implanted in rat spinal cord complete T3 transection sites. This is the most severe model of SCI and the most challenging model for the study of spinal cord regeneration. It is also a model to study axon regeneration since axons are severed upon injury, unlike contusion where there is a rim of spare tissue with surviving axons, which makes it difficult to determine if observed axons are truly regenerating axons or are spared or sprouting axons. Nineteen Fischer 344 rats underwent T3 complete spinal cord transections and immediate placement of a 2 mm-long implant into the lesion site. Eight control animals had the lesion only. Four weeks later, spinal cords were removed and implant structure, biocompatibility, and axonal regeneration/remyelination were assessed. Findings were compared to animals that previously received templated agarose implants with the same lesion and survival time.

Figure 4:
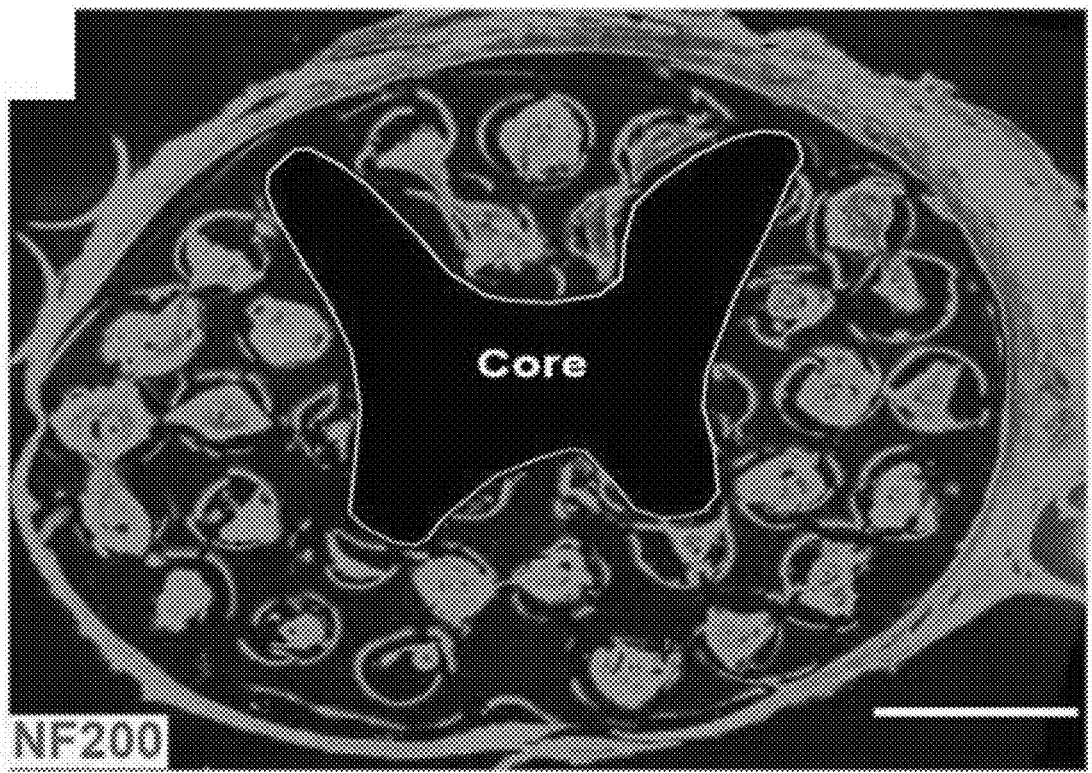
FIG. 4 depicts a 3D printed implant implanted into a spinal cord injury site, four weeks after implant implantation.
Figure 19:
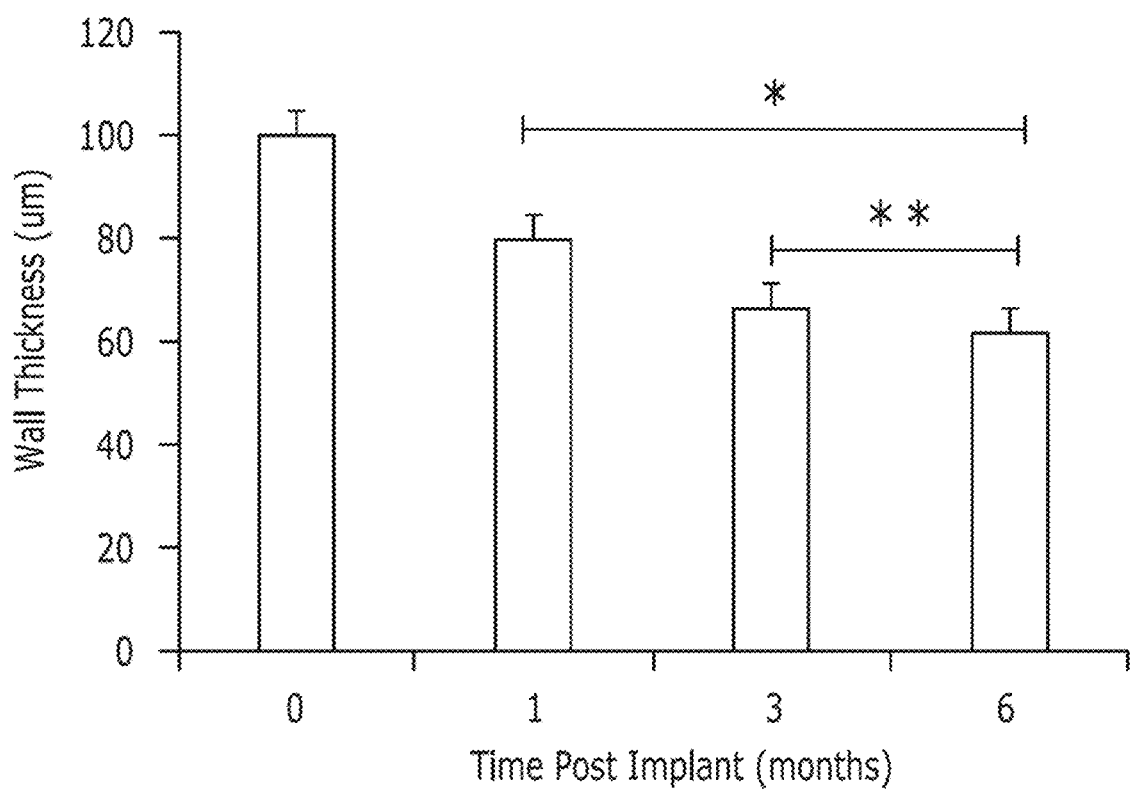
FIG. 19 depicts implant degradation measured by reduction in wall thickness. *p<0.0001, **p<0.001. (ANOVA; post-hoc Tukey's).

Four weeks after implantation, 3D printed PEGDA/GelMa implants maintained structural integrity: the channels and solid core of the implant retained their pre-implantation structure without breakage or deformation in all animals (FIG. 4). Implant biodegradation was not yet evident at this four-week time point. Earlier efforts using other implant materials such as hyaluronic acid resulted in more rapid implant degradation and collapse of the structure (FIG. 18A-D). Implant degradation was characterized over 6 months showing a reduction of 44 μm in wall thickness, representing preservation of 66% of structure (FIG. 19). Maintenance of implant structure over is considered essential to retain physical support across a lesion site and to support, organize and align the growth of regenerating axons.

Figure 14A:
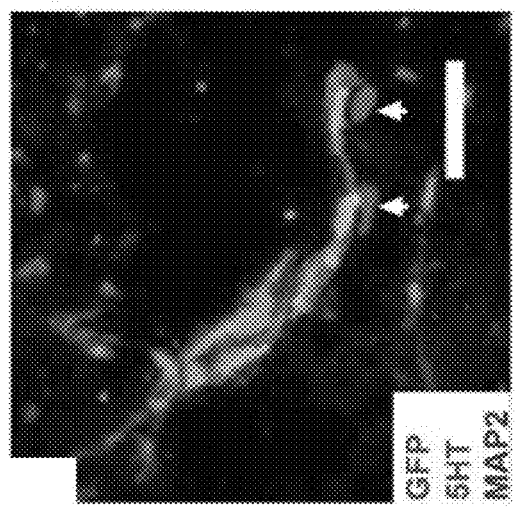
FIGS. 14A-B depict printed implants loaded with neural stem cells, four weeks after implantation.
Figure 14B:
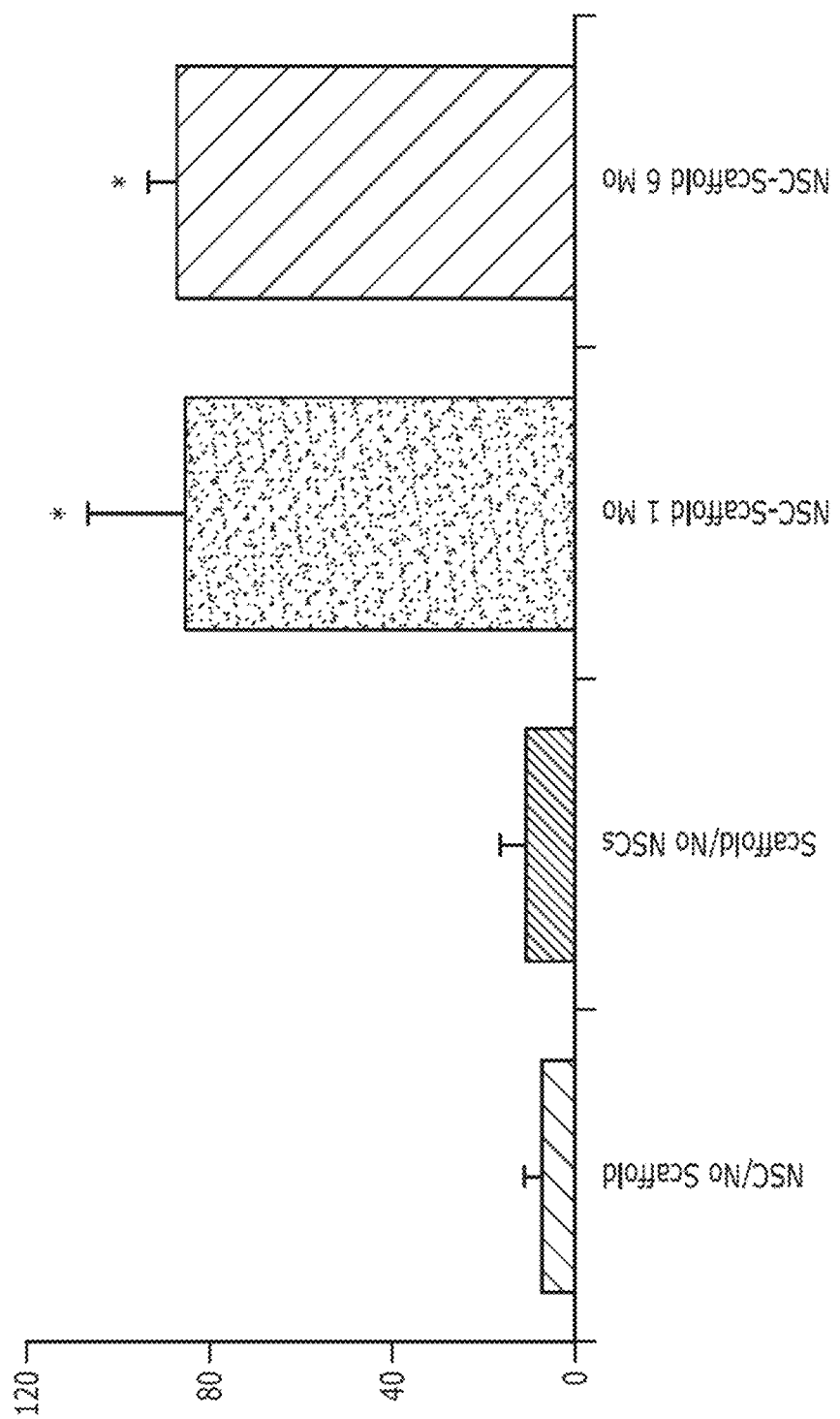
Figure 15A:
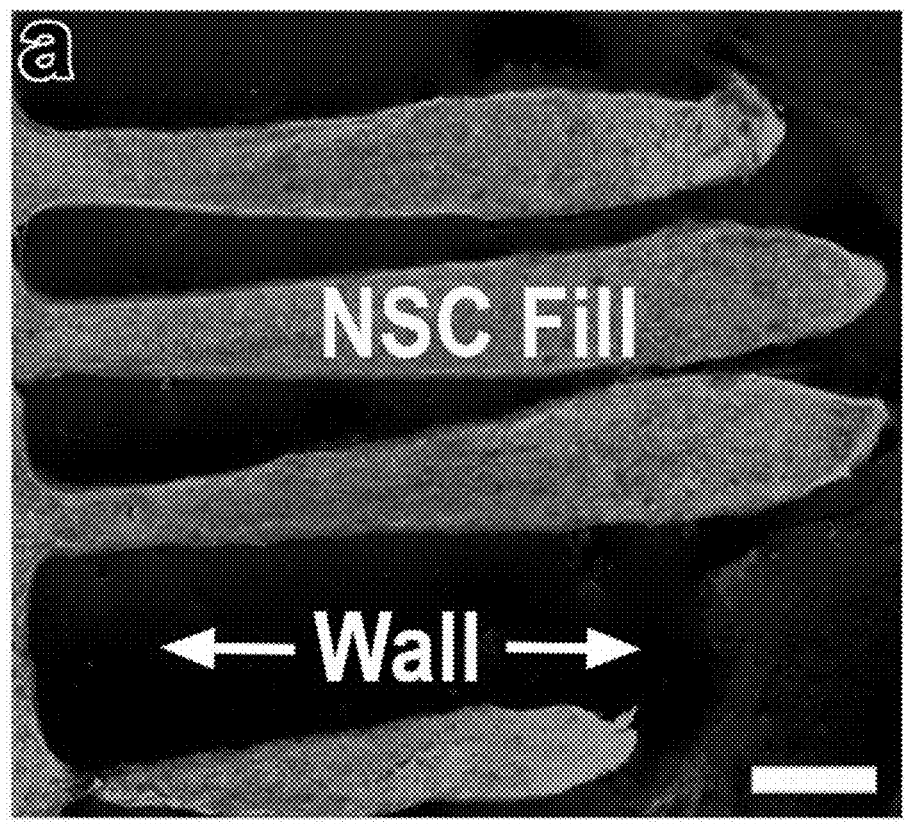
FIGS. 15A-G depict printed implants loaded with neural stem cells in long-term in vivo studies.
Figure 15B:
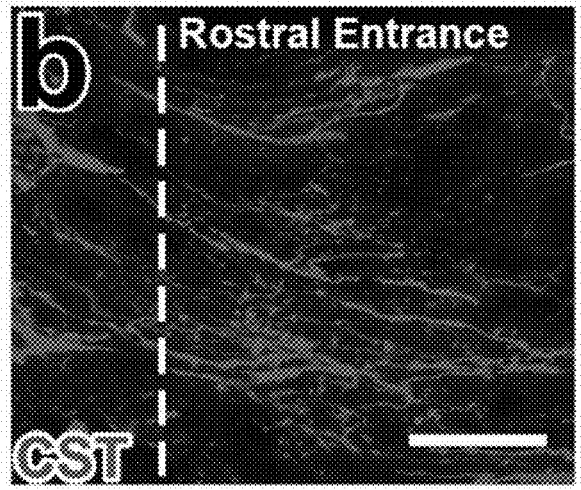
Figure 15C:
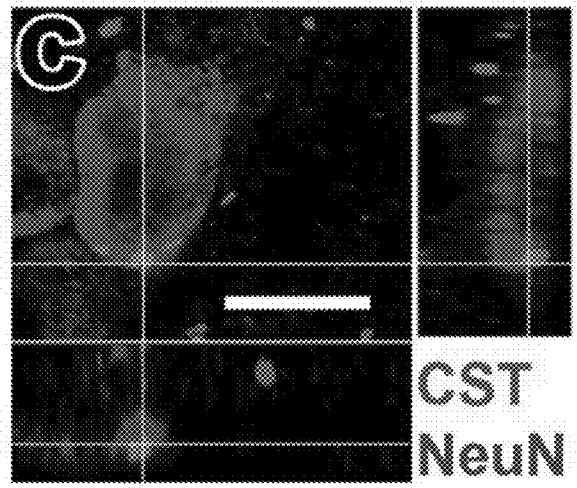
Figure 15D:
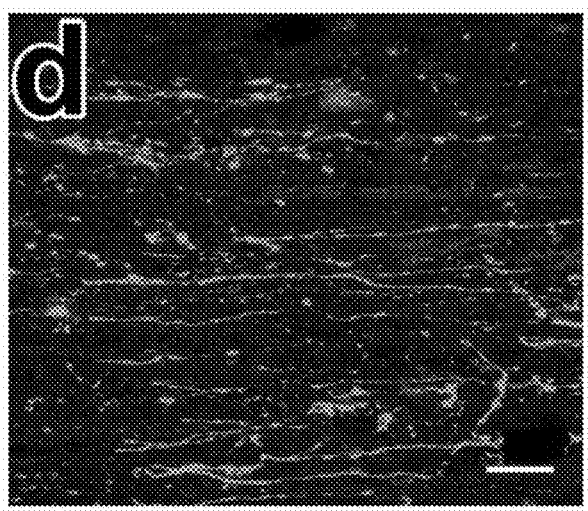
Figure 15E:
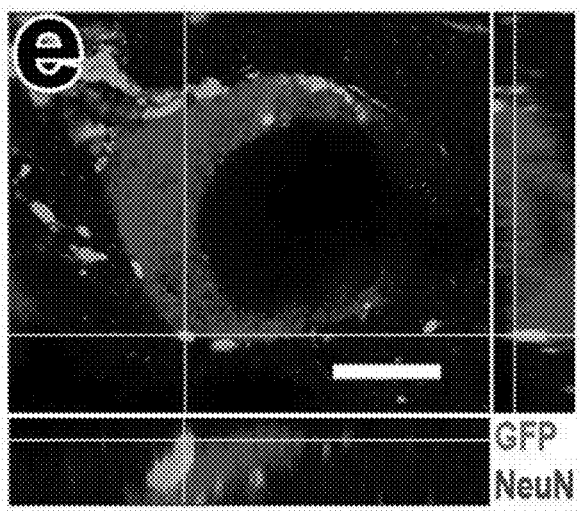

Anatomical analysis six months later showed that all implants retained their 3D architecture (FIG. 15A); however, the thickness of implant walls was reduced by 49% compared to their pre-implantation size, suggesting slow degradation over time. Among animals implanted with empty implants, host neurofilament-labeled axons regenerated into implants in relatively modest numbers (118±8), similar to numbers observed four weeks after implantation (97±8 axons). In no case did host axons regenerate beyond the implant and into the distal host spinal cord in animals implanted with empty implants. Among animals implanted with 3D biomimetic PEGDA/GelMa implants loaded with neural stem cells, grafted cells survived through the six-month period and completely filled all channels (FIG. 15). Nestin labeling was not detected, indicating completion of maturation of the implanted neuron stem cells, and Ki67 labeling was also not detected, indicating completion of cell division by grafts. As observed in 4-week implants, 5HT-immunoreactive axons entered the implant. 87±5 serotonergic axons reached the caudal end of channels loaded with neural stem cells, and continued to regenerate into the caudal spinal cord, similar to the number of axons observed four weeks after implantation (FIG. 14B); this observation suggests that serotonergic axon regeneration into implants is complete by four weeks. Host corticospinal motor axons, anterogradely labeled by injections of AAV2 vectors expressing red fluorescent protein (RFP) into the motor cortex, also regenerated into stem cell-loaded implants (FIG. 15B) and extended to implant midpoints, a distance of 1 mm. Corticospinal axons formed putative bouton-like structures on NeuN labeled neurons within the implant channels (FIG. 15C). Moreover, graft-derived GFP-labeled axons projected out from the implants and into the host spinal cord caudal to the injury, forming putative bouton-like structures on host neurons in the spinal cord caudal to the lesion (FIG. 15D-E). The amount of graft-derived axonal outgrowth from implants into the distal host spinal cord (FIG. 15D) greatly exceeded the number of host serotonergic axons regenerating beyond the implant; this observation suggests that restored neural relays across the lesion site, if present, can be mediated by host axons regenerating into the implant, synapsing onto grafted neural stem cells, and stem cell-derived axons extending into the distal host spinal cord.

Figures 5A, 5B, 5C:
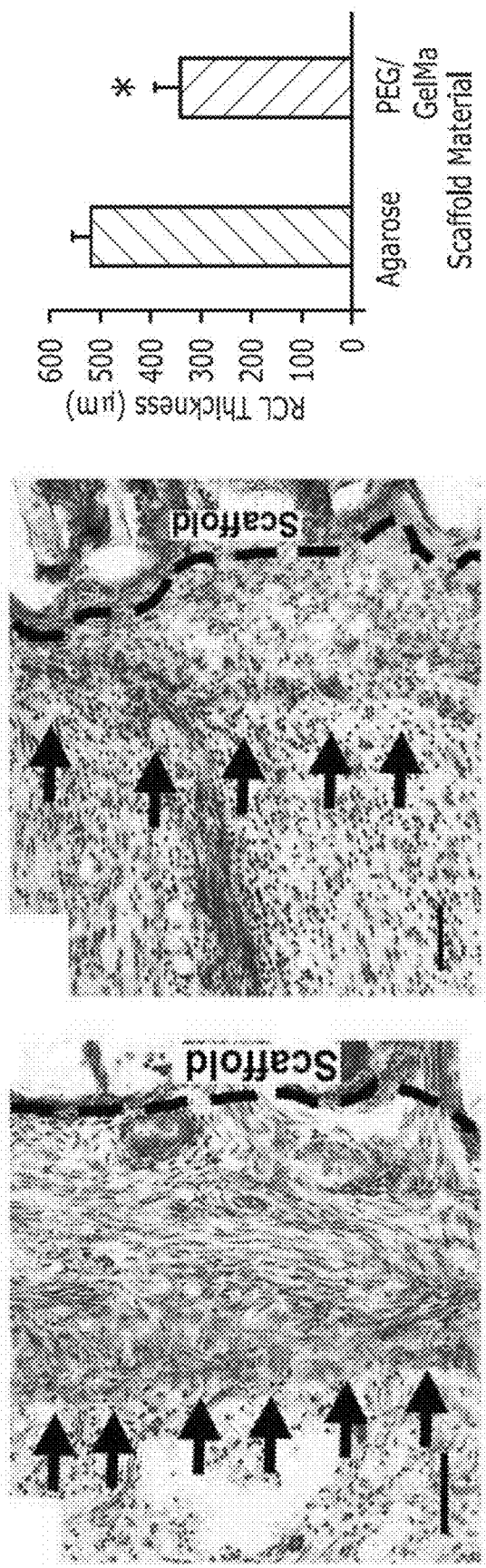
FIGS. 5A-C depict 3D printed implants implanted into spinal cord injury sites four weeks after implantation. Depicted is Nissl staining of the implant site (site of a T3 complete transection) reveals a reactive cell layer (arrows) at the site of implantation of an agarose scaffold (FIG. 5A), which is substantially attenuated after implantation of a 3D printed polyethyene glycol diacrylate/gelatin methacrylol (PEGDA/GelMa) implant disclosed herein (FIG. 5B). The scale bar is 200 μm. Rostral is to the left, caudal to the right. The interrupted line demarcates the interface of host spinal cord with the implant.
Figures 7A, 7B:
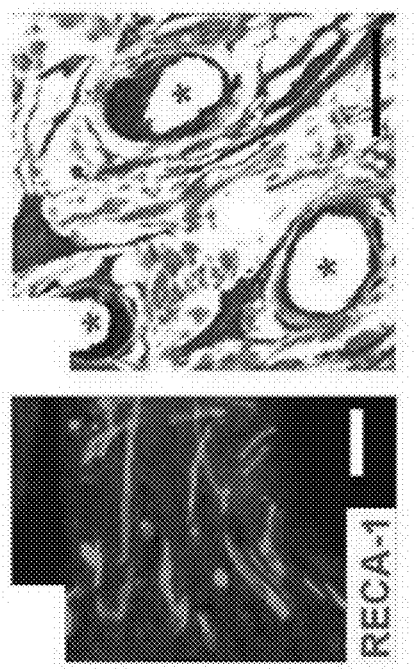
FIGS. 7A-B depict 3D printed implants implanted into spinal cord injury sites four weeks after implantation. Implants are well-vascularized (RECA-1 immunolabeling for blood vessels) (FIG. 7A) and toluidine blue stain shows blood vessels (asterisks) (FIG. 7B). The scale bar for FIG. 7A is 25 μm and 20 μm for FIG. 7B.

Attenuation of the reactive cell layer existed among animals that received 3D printed implants compared to templated agarose scaffolds, characterized by reduced collagen deposition (FIG. 4B) and reduced granularized tissue (FIG. 5A). The reactive cell layer was 340±52 μm thick, a significant reduction of 35% compared to agarose scaffolds (P<0.05; FIG. 5A). Astrocyte responses were also attenuated by 3D printed implants: in control lesion subjects, astrocytes became reactive and "walled off" the lesion site (FIG. 6A). In animals with agarose scaffolds, astrocyte walls were still present and walled off the scaffold from the host spinal cord (FIG. 6B). In contrast, 3D printed implants exhibited an attenuation of the thickness of the astrocyte scar and a reorganization of the scar such that it no longer interrupted continuity from the host spinal cord into implant channels (FIG. 6C). In some embodiments, astrocyte processes turned from forming a perpendicular wall at the interface with the host to forming strands that penetrated the implant linearly, with which regenerating host axons became associated. Three-dimensional printed implants exhibited a 66% reduction in astrocyte immunoreactivity compared to agarose scaffolds, and a 97% reduction compared to lesion-only animals (P<0.05; FIG. 6D). implants became readily and extensively vascularized along their entire length (FIG. 7A-B).

Figure 8B:
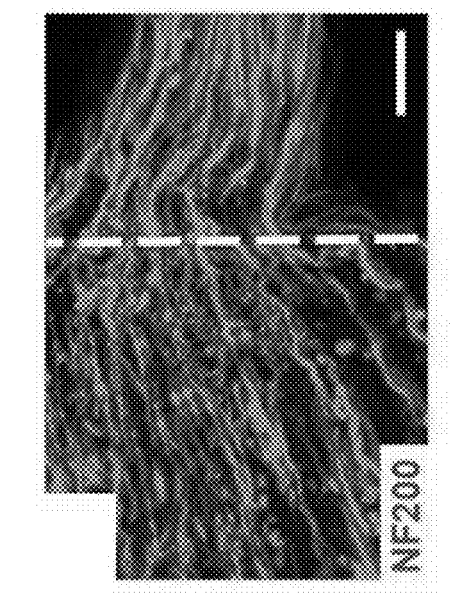
FIGS. 8A-B depict 3D printed implants implanted into spinal cord injury sites four weeks after implantation. NF200-labeled host axons fail to cross a scar that is present around agarose scaffolds (FIG. 8A), yet readily penetrate the 3D printed implant (FIG. 8B). The scale bar is 100 μm. The dashed line indicates implant entrance from rostral aspect of lesion site.
Figure 8A:
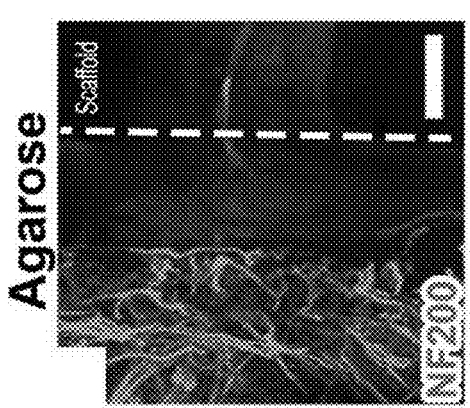
Figure 9A:
FIGS. 9A-C depict 3D printed implants implanted into spinal cord injury sites four weeks after implantation.
Figure 9B:
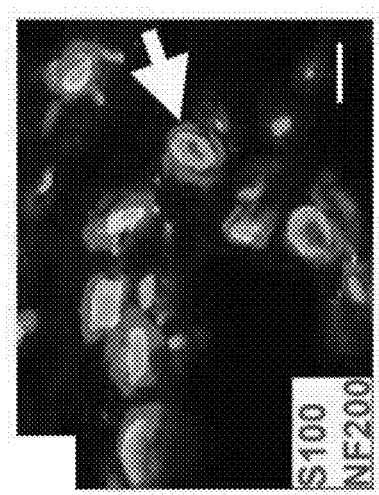
Figure 9C:

In accordance with the reduction in the thickness of the reactive cell layer, host axons approaching the 3D printed implant were aligned along the rostral-caudal (descending) axis of the spinal cord, and readily penetrated the channels of the implant without deflection; this was in contrast to frequent axonal misalignment and deflection that occurred at the interfaces of agarose scaffolds with the host (FIG. 8A-B). Host Schwann cells from the peripheral nervous system migrated into the implants and ensheathed or remyelinated regenerating host axons (FIG. 9A-C).

In some embodiments, implants for spinal cord repair described herein can be loaded with cells that can enhance regeneration or remyelination. Thus, 3D printed implants were loaded with GFP-expressing rat neural stem cells taken from embryonic day 14 spinal cords of Fischer 344 rats. A total of $3 \times 10^6$ cells were loaded into implants in a volume of 8 μl by direct injection. A total of 14 rats underwent T3 spinal cord complete transection, removing a 1.8 mm-long spinal cord segment and implanting a 2 mm-long 3D printed implantloaded with neural stem cells. Animals survived four weeks and were sacrificed to assess implant integrity, cell survival and host axon regeneration and remyelination.

Figures 21A, 21B, 21C, 21D:
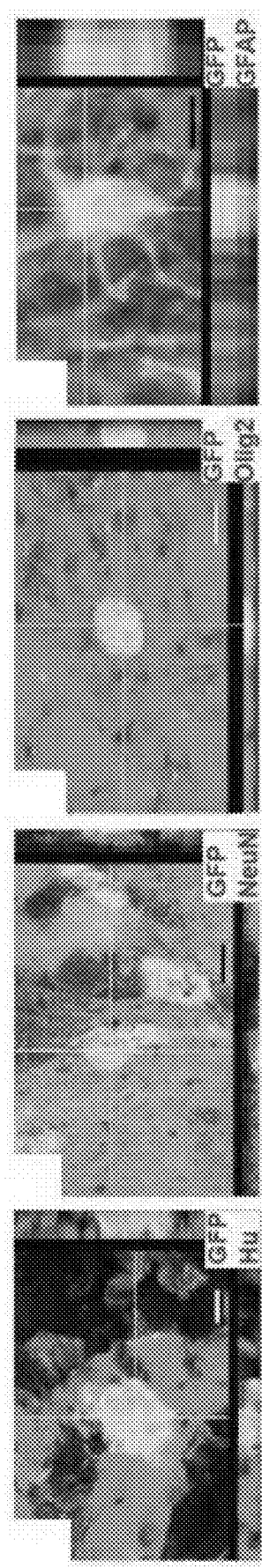
FIGS. 21A-B depicts stem cell-derived cells in the channels expressing either the neuronal marker Hu (FIG. 21A) or NeuN (FIG. 21B), in addition to GFP. The scale bar is 5 μm.
FIG. 21C depicts that they also express the oligodendrocyte marker Olig2, together with GFP.
FIG. 21D illustrates that the astrocyte marker GFAP, together with GFP. The scale bar is 5 μm.

In some embodiments, stem cells survived in every grafted animal and filled the implant channels (FIG. 10A, FIG. 20A-D). Neural stem cells were also present at interfaces between the implants and host spinal cord, without distorting implant or host spinal cord architecture (FIG. 20A-D). Of the samples tested, 47±2% of grafted stem cells expressed the early neuronal marker Hu (FIG. 21A), 20±3% of grafted cells expressed the mature neuronal marker NeuN (FIG. 21B), 11±2% of cells expressed the oligodendrocyte marker Olig2 (FIG. 21C), and 21±3% of cells expressed the astrocyte marker GFAP (FIG. 21D and 22). The stem state marker Nestin was not detected.

Figure 10C:
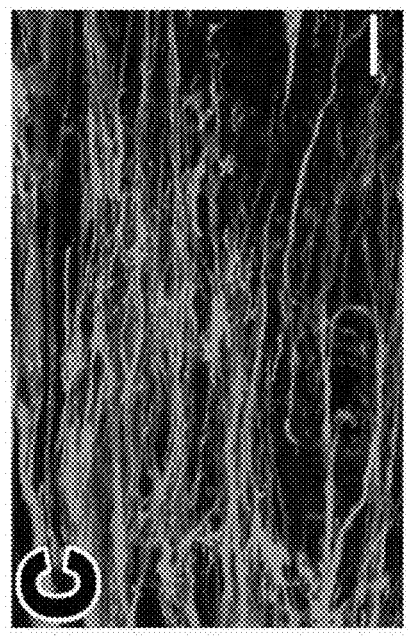
Figure 10B:
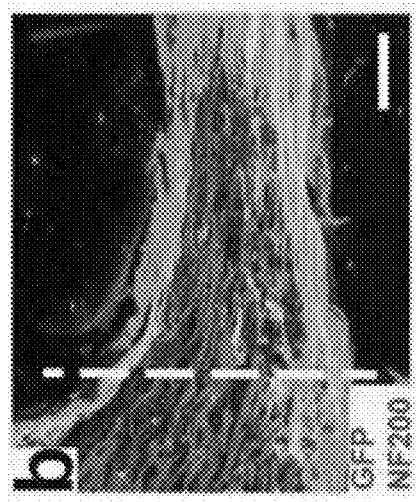
Figure 10A:
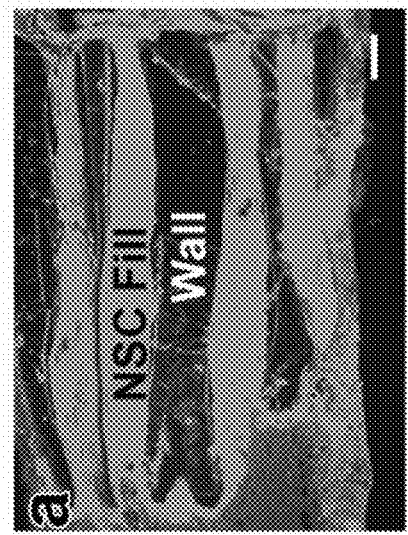
Figure 10H:
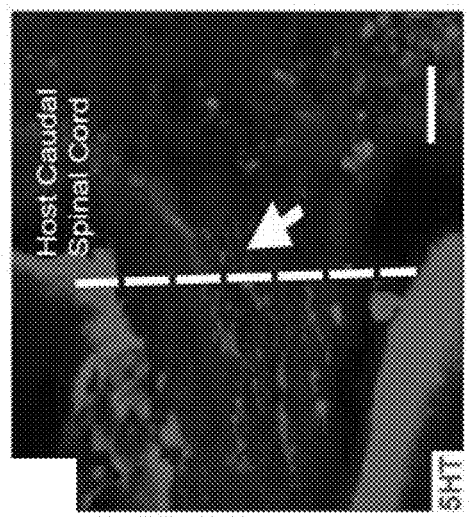
Figure 24B:
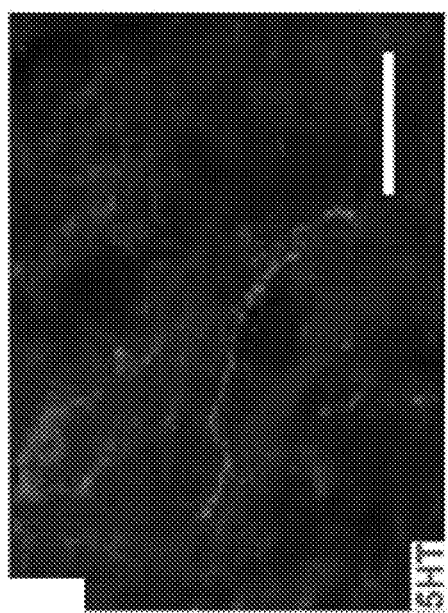

Host axons readily penetrated implants (distinguished from grafted-derived axons by an absence of GFP reporter expression) (FIG. 10B). Many host long-tract serotonergic axons also readily penetrated 3D printed implants loaded with stem cells and linearized in accordance with the channels orientation (FIG. 10C). A stem cells graft was not able to linearize penetrating axons (FIG. 23). 5HT axons were guided to regenerate to the caudal ends of the implants (FIG. 10E). In contrast, few serotonergic axons reached the caudal end of empty implants (lacking stem cell fills) or a stem cells graft. (FIG. 24A-B). A mean of 85±21 serotonergic axons were quantified within the caudal 400 μm of stem-cell loaded channels per implant per animal, compared to 11±5 axons in empty 3D printed implants. A mean of 8±4 axons serotonergic axons reached the end of the lesion site in animals with stem cell grafts lacking implants, a 10-fold reduction in the number of axons compared to implants containing stem cell grafts (P<0.05 ANOVA, P<0.05 post-hoc Tukey's comparing implants with stem cells to implants without; FIG. 10F). Thus, 3D printed implants containing neural stem cells can, in some embodiments, enhance host axon regeneration to the caudal end of a lesion site. In other embodiments, this enhancement can be significant and substantial.

Figure 10G:
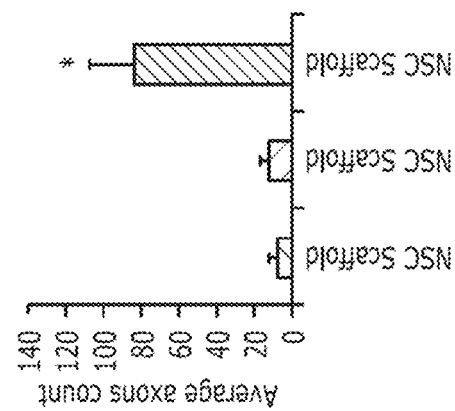
Figure 10F:
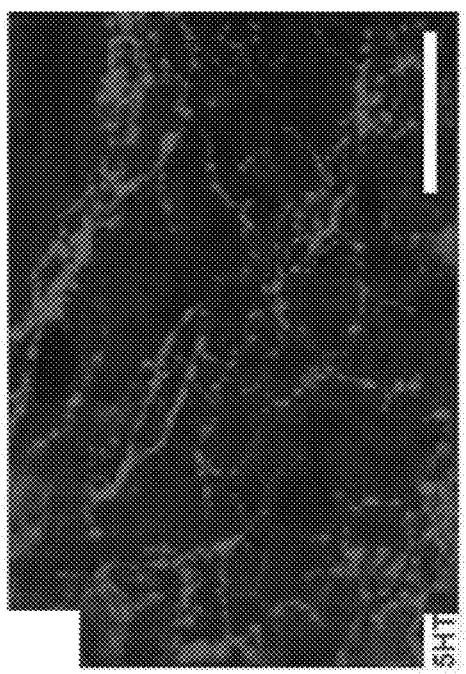
Figure 26A:
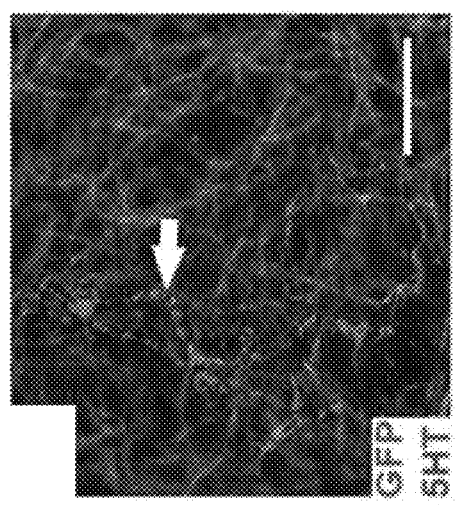
FIGS. 26A-C depict (K1, scale bar is 100 μm) 5HT-labeled motor axons are visible in the host spinal cord caudal to the lesion in host gray matter (FIG. 26A), (K2, scale bar is 50 μm) host white matter (FIG. 26B), and (K3, scale bar is 25 μm) crossing from white into gray matter. NF200 staining for host axons are visible (FIG. 26C).
Figure 25:
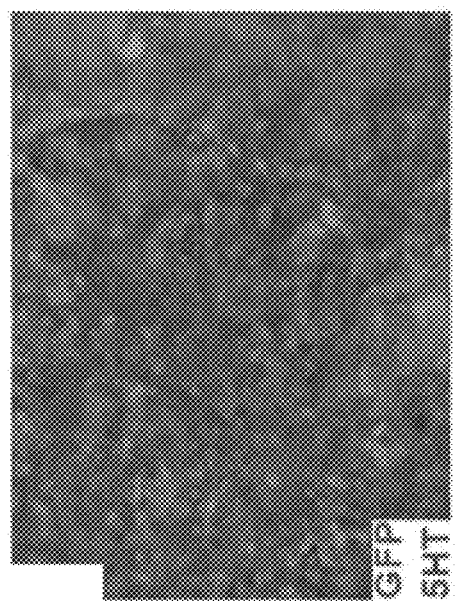
FIG. 25 depicts 3D rendering of 10 μm z-stack of 5HT-labeled host motor axons inside a channel did not co-label with GFP, indicating that there are no serotonergic neuronal cell bodies in the spinal cord-derived neural stem cell grafts.
Figure 27A:
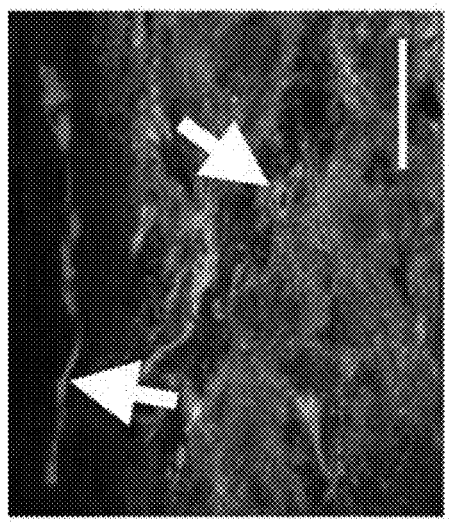
FIGS. 27A-B depict a single channel of 3D printed implant loaded with neural stem cells, demonstrating vascularization. GAP43 labeled axon inside a channel loaded with GFP expressing NSCs (FIG. 27A, scale bar is 25 μm). GAP43 labeled axons in host spinal cord, caudal to the implant (FIG. 27B, scale bar is 25 μm).
Figure 26C:
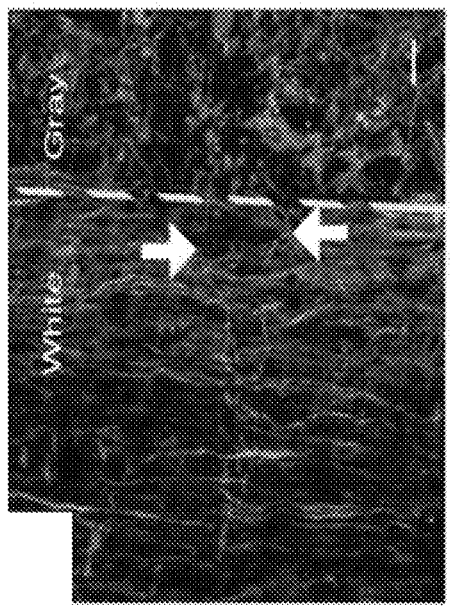
Figure 26B:
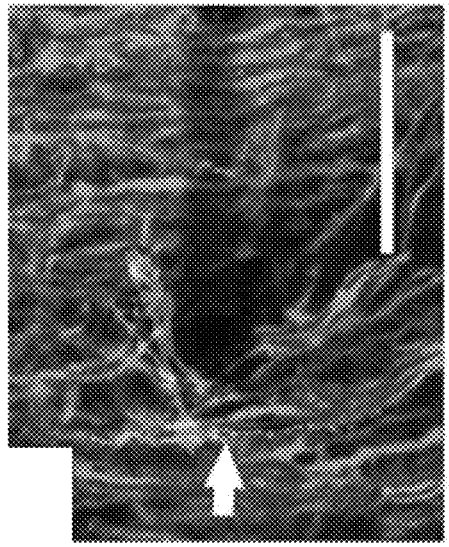
Figure 27B:
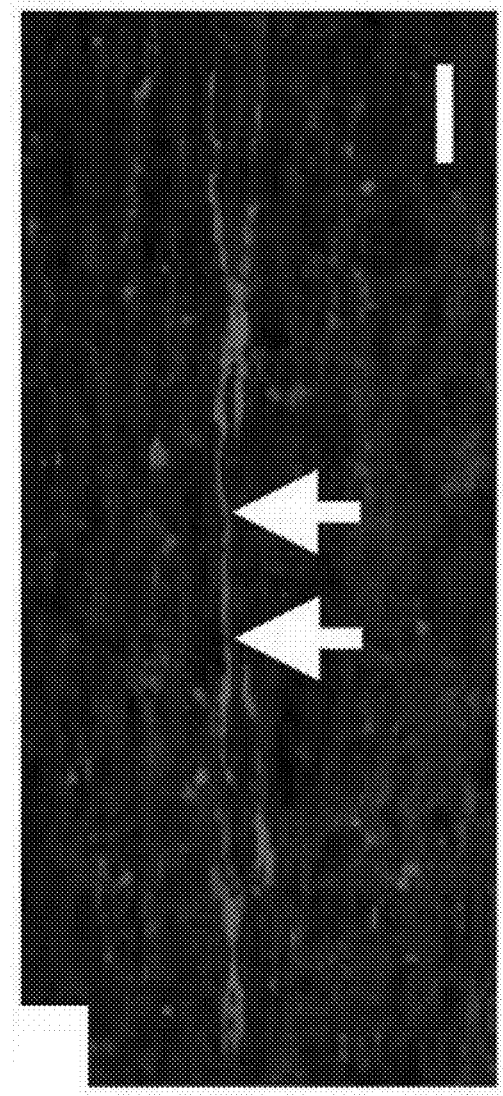

In some embodiments, host serotonergic motor axons regenerated completely through the lesion site/implant and re-entered the caudal spinal cord (FIG. 10G). Serotonergic axons located in the host spinal cord caudal to the lesion were not graft-derived, since neural stem cells in the implant did not immunolabel for 5HT (serotonin) and these axons did not label for GFP (FIG. 25). There, 2 mm beyond the caudal edge of the implant, serotonergic axons were detected in the white and gray matter of the host spinal cord and frequently branched to enter gray matter (FIG. 26A-C). Host long-tract serotonergic axons were detected up to 3.5 mm beyond the lesion site (FIG. 10H), but not beyond, further supporting the fact that these were regenerating axons. In some embodiments, the present implants and devices can provide host motor axon regeneration into and beyond implants implanted in complete spinal cord transection sites. Regeneration was further demonstrated by the presence of GAP43 immunolabeled axons in the channels and host caudal spinal cord (FIG. 27A-B).

Figure 11:
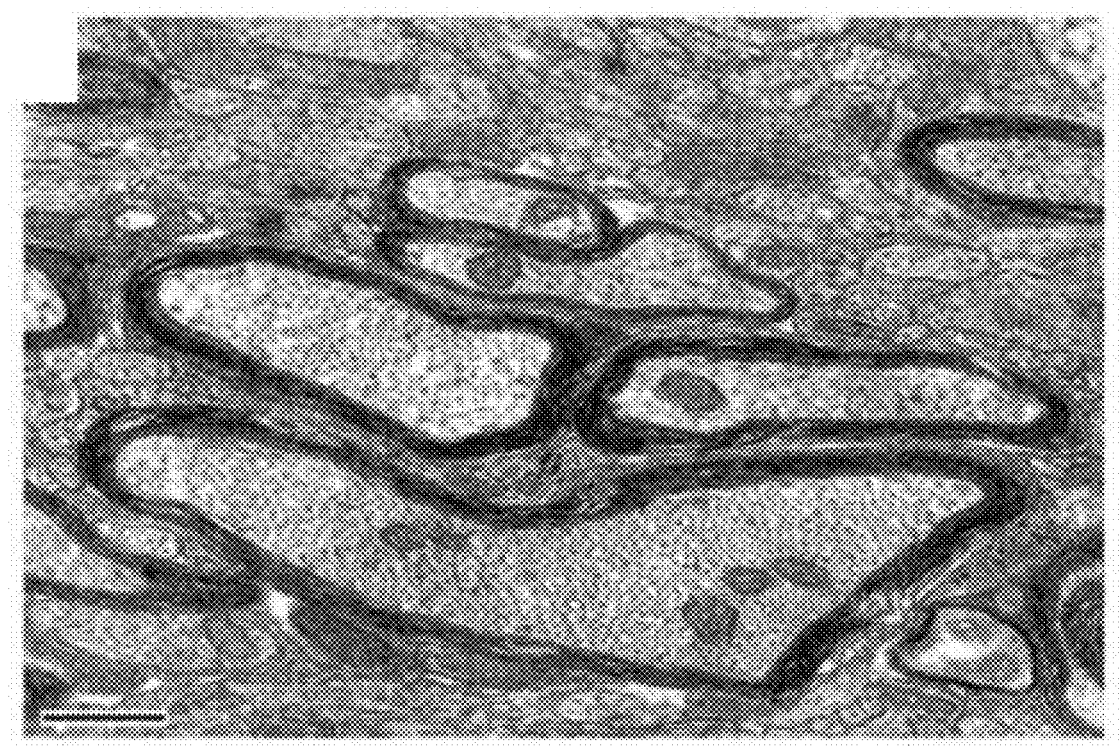
FIG. 11 depicts at an ultrastructural level, axons of varying diameters are present within channels and many axons are myelinated after implantation of the implant of FIG. 10. The scale bar is 500 μm.
Figure 12B:
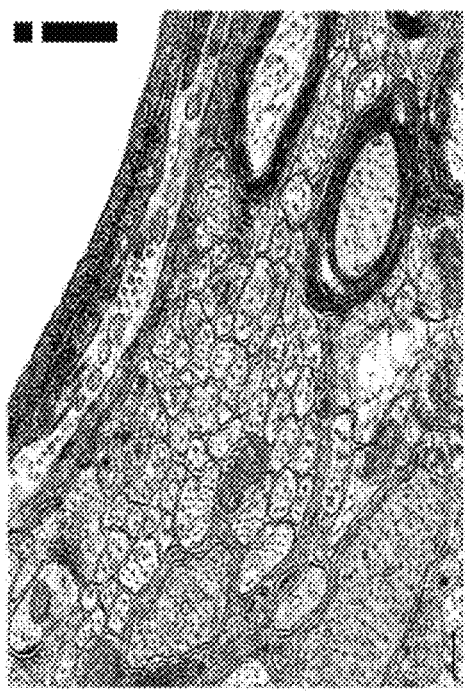
FIGS. 12A-B depict ultrastructural analysis of implant sites four weeks after implantation.
Figure 12A:
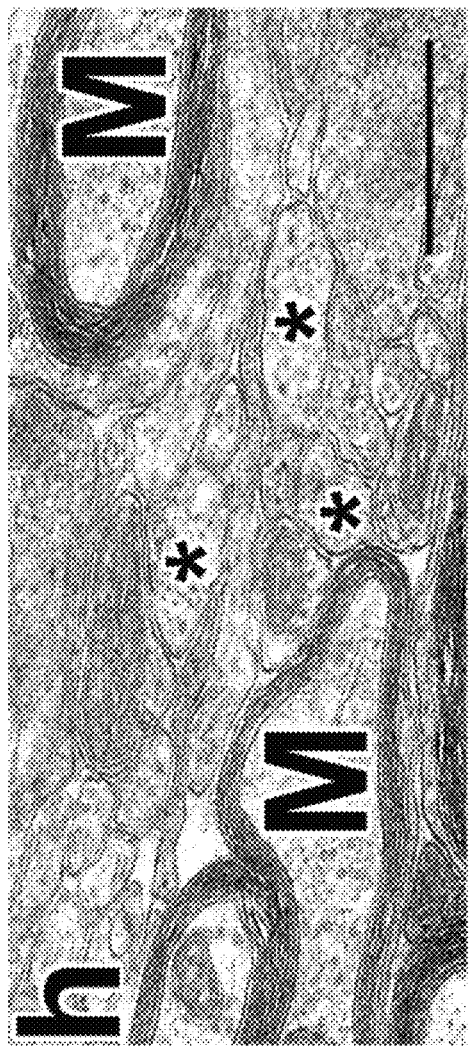
Figure 13:
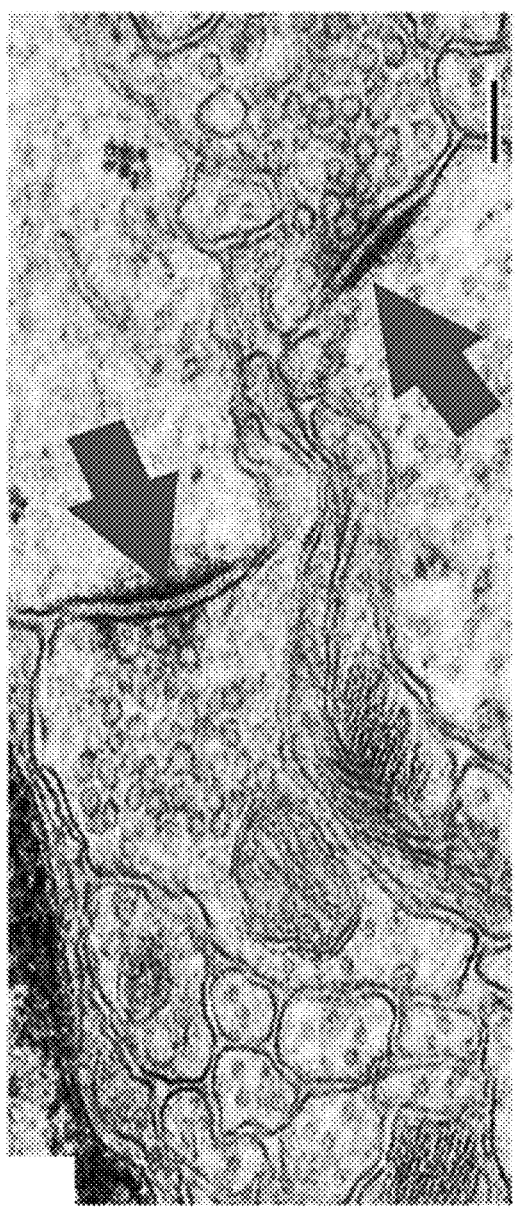
FIG. 13 depict printed implants loaded with neural stem cells, four weeks after implantation. Synapses (arrows) are formed between axons within channels and the dendrites of implanted neural stem cells. The scale bar is 200 μm. Synapses are asymmetric and pre-synaptic boutons contain rounded vesicles, indicating that these are excitatory.
Figure 28A:
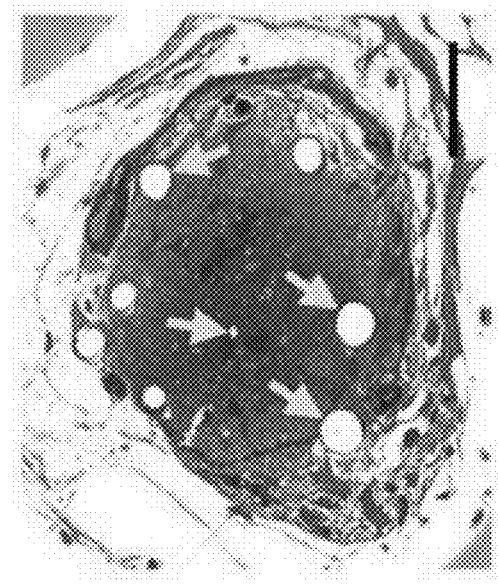
FIGS. 28A-B depict toluidine blue stain, arrows point to blood vessels (FIG. 28A, scale bar is 100 μm). EM image, the blood vessel is labeled with an asterisk (FIG. 28B, scale bar is 1 μm).
Figures 28B, 29, 30:
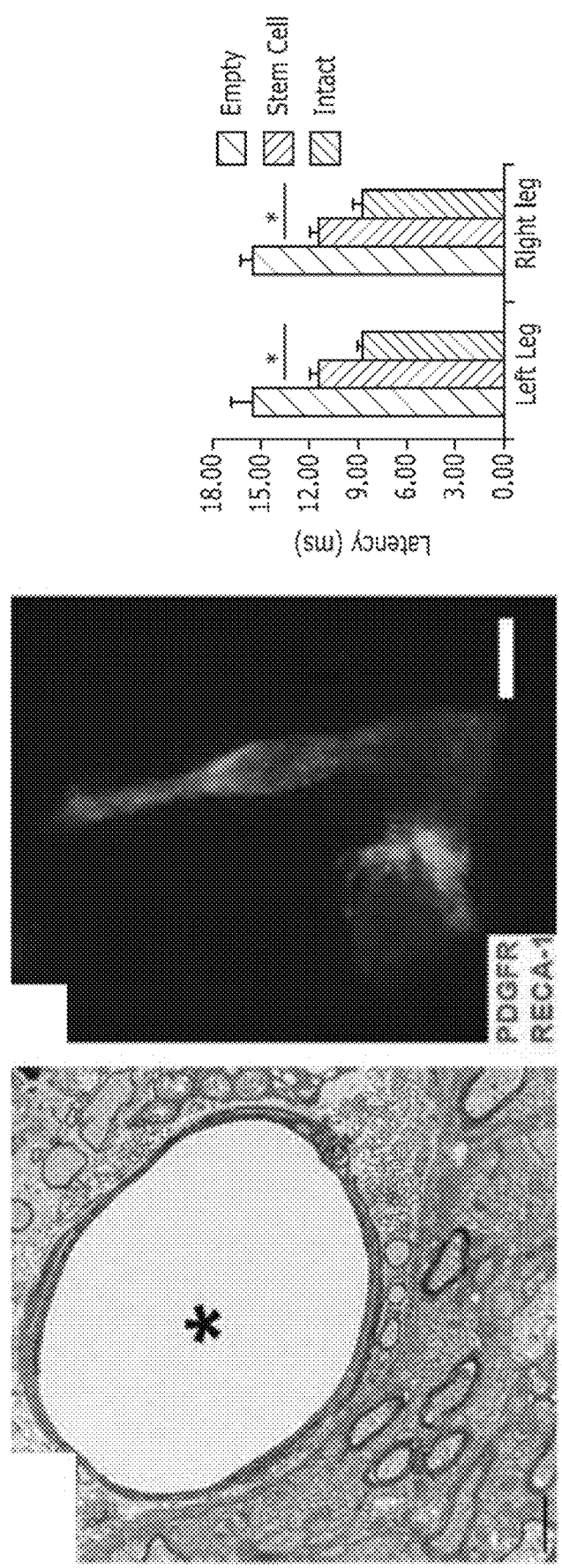
FIG. 29 depicts PDGFR labeling for pericytes revealed them surrounding RECA-1 labeled blood vessels indicating BBB restoration. The scale bar is 15 μm.
FIG. 30 depicts that MEPs latency was shorter in animals implanted with stem cell implants relatively to empty implant treated animals, and was close to the latency observed in intact animals (p<0.01).
Figure 31:
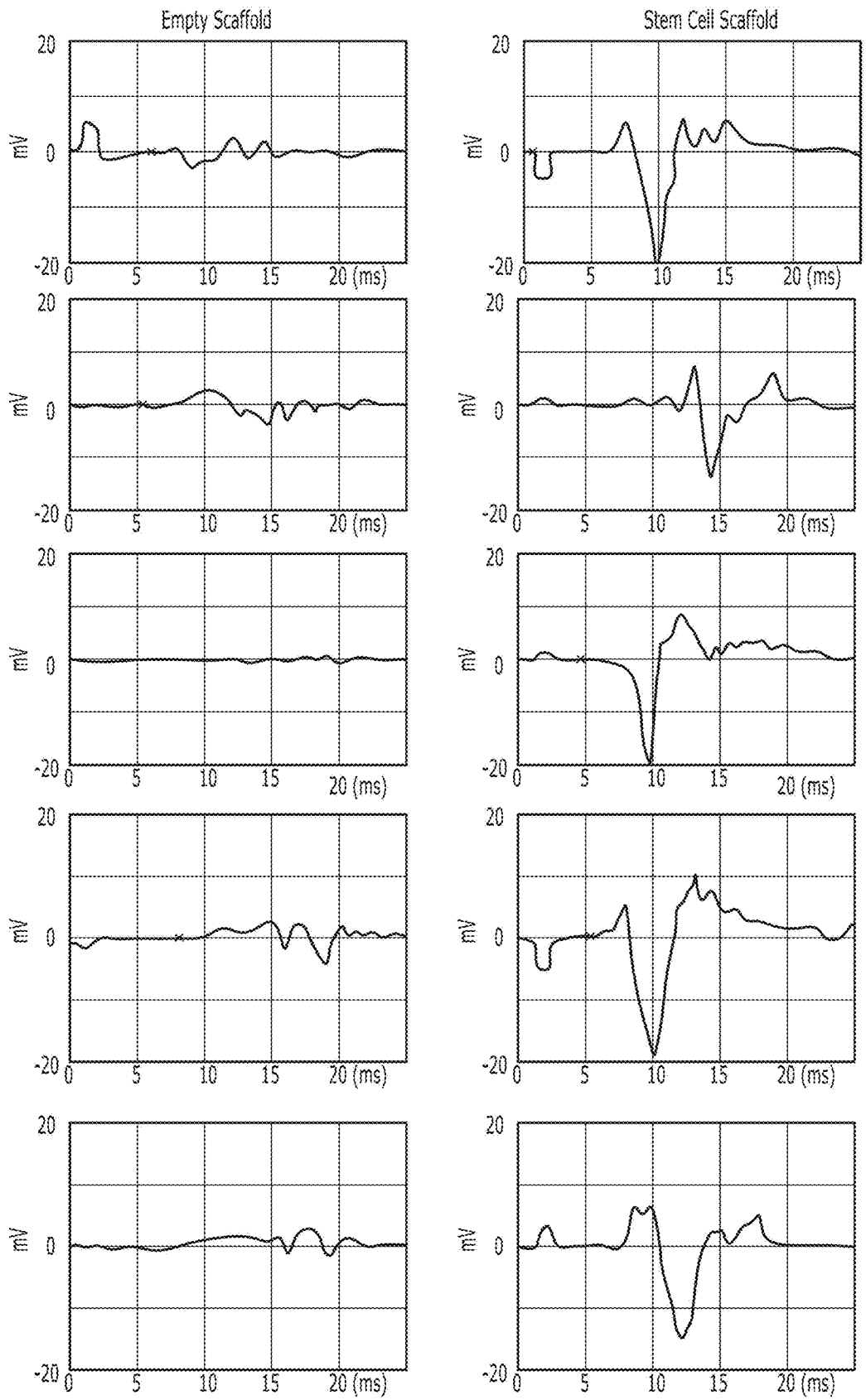
FIG. 31 depicts motor-evoked potential recordings from animals receiving implants with and without stem cells.
Figure 32A:
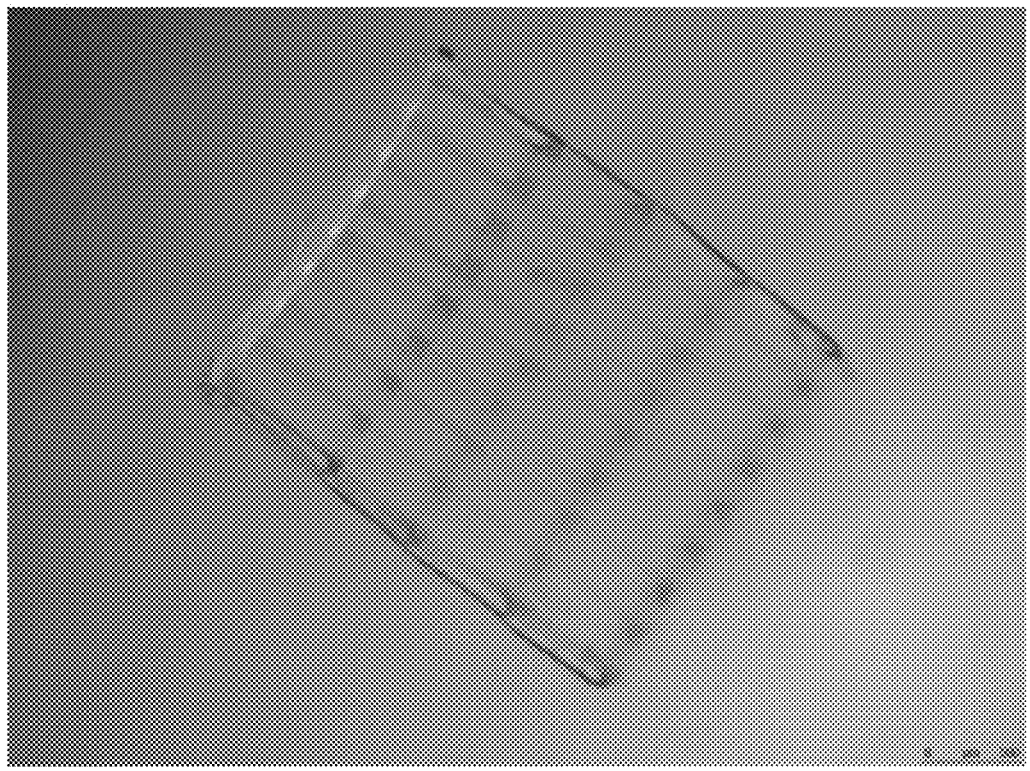
FIG. 32A depicts a implant including linear channels.
Figure 32B:
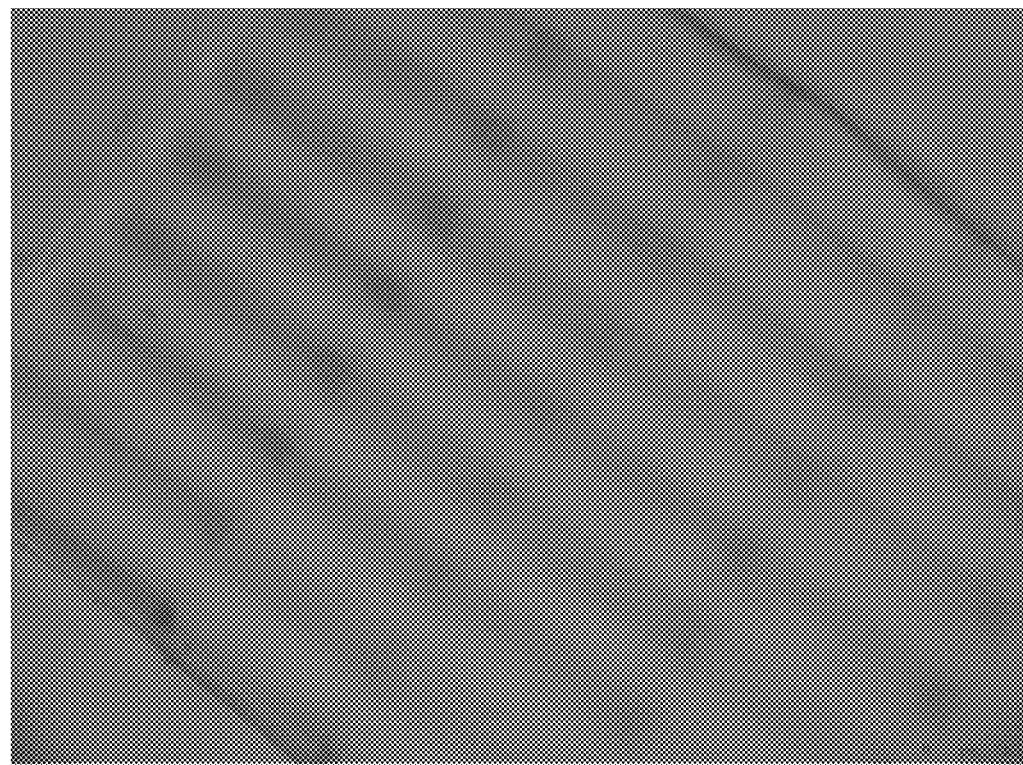
FIG. 32B is a zoomed-in version of FIG. 32A.
Figure 33A:
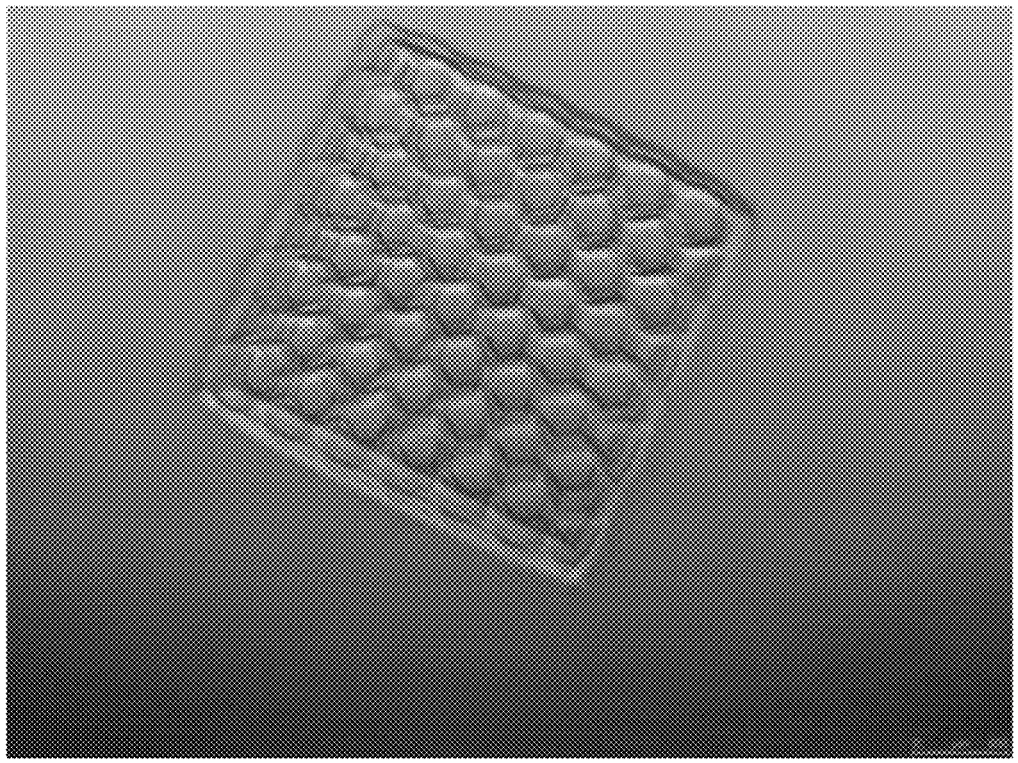
FIG. 33A depicts a implant including a honeycomb structure of linear channels packed together.
Figure 33B:
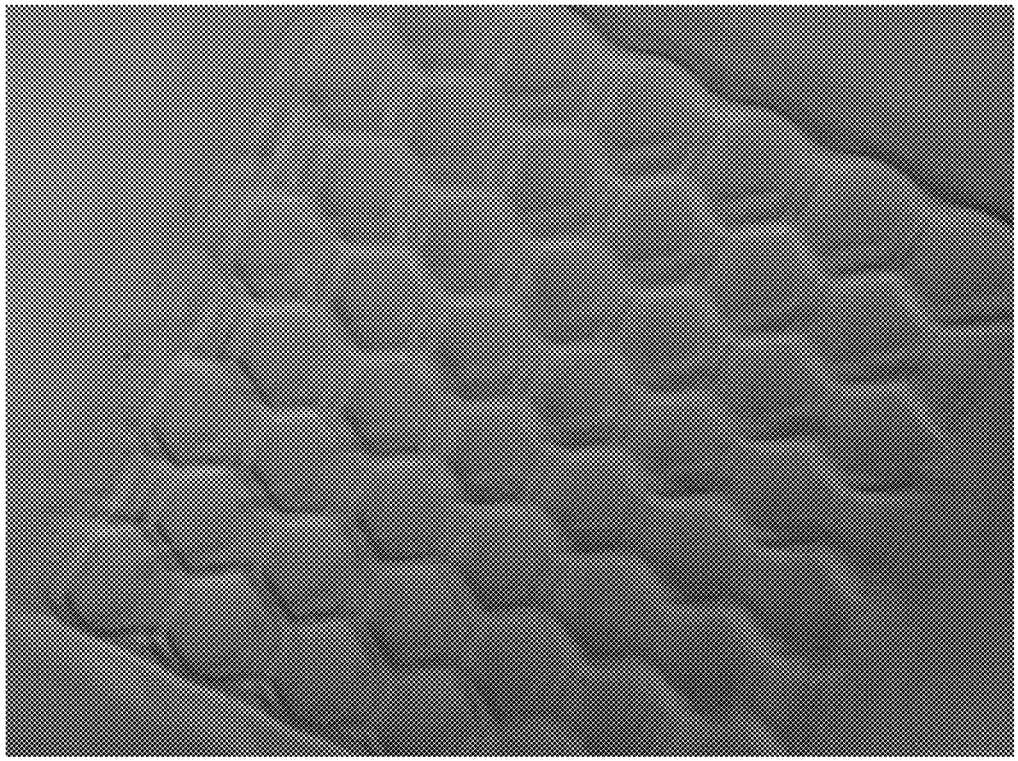
FIG. 33B is a zoomed-in version of FIG. 33A.

In some embodiments, an obstacle of tissue engineering is organ vascularization. Toluidine blue and electron microscopic analysis demonstrated extensive vascularization within implant channels (FIG. 28A-B) described herein. The presentation of platelet-derived growth factor receptor (PDGFR) immunolabeling around those blood vessels confirmed the presence of pericytes and restoration of the blood-brain barrier (FIG. 29). Electron microscopic analysis of axons in neural stem cell-filled channels demonstrated a range of axon calibers and myelination states, from small, unmeylinated axons (<1 µm diameter) to large, myelinated axons (1-3 µm, FIG. 11). Toluidine blue stain showed oligodendrocytes myelinated those axons (FIG. 12). Because implants were loaded with neural stem cells that expressed the mature neuronal marker NeuN, the potential existed for the formation of synapses between regenerating host axons and neurons in implant channels. In some embodiments, asymmetric synapses were readily observed that received inputs from axons containing rounded synaptic vesicles, typical of excitatory synapses (FIG. 13). Host serotonergic axons regenerating into channels can be closely associated with dendrites of stem cell-derived neurons, identified by co-labeling for MAP2 and GFP (FIG. 14), also suggesting synapse formation.

Functional and behavioral outcomes were measured using two independent tests. Twenty-six weeks post implant an electrophysiological study was performed by applying transcranial electric stimulation to the motor cortex and motor evoked potentials (MEP) from the hindlimbs were recorded. MEP can be used to test electrophysiological regain of function (in both humans and animals) to test supraspinal control of the brain on the peripheral nervous system by recording EMG signals from muscles. Twenty-six weeks post injury rats implanted with 3D printed implants loaded with neural stem cells exhibit recovery of MEP responses that was abolished upon re-transection of the spinal cord at the C8 spinal level (above the implant site; T3). These data are indicating that muscle activity in the hindlimbs was generated by synaptic transmission from the host across the implant (FIG. 15A-E, FIG. 31). Thus, in some embodiments, the described implants can provide synaptic transmission from the host across the implant to provide muscle activity in the hindlimbs.

Since the hindlimbs were denervated and the animals were not supporting the weight on them, the muscles became atrophied, and there were less muscle units that can respond. This explains the difference in magnitude between the intact to experimental animals(FIG. 15A-E). Consistent with this observation, the amplitude of MEPs was significantly greater than animals with empty implants (p<0.05, FIG. 15E). In addition, the latency of recorded MEPs (time to the maximum amplitude) was shorter in stem cell implants and was closer to the intact latency observed (ANOVA p<0.01, FIG. 30).

To determine the extent of motor functional recovery by 3D biomimetic PEGDA/GelMa implants, animals were assessed using the Beattie Basso Bresnahan (BBB) locomotor scale over a 6-month period, until behavior plateaued and was stable. Animals that received implants loaded with neural stem cells exhibited significant functional recovery compared to animals with empty implants.

Hindlimb locomotion was impaired (e.g., severely) in both lesion control and grafted subjects for the first four weeks post-injury. In the fifth week, recipients of implant loaded with NSCs begun showing improvement on the BBB scale, reaching a level of 7, indicating movement about each joint of the hindlimb, in contrast to minimal movement if any in lesioned controls (repeated measures ANOVA p<0.01; individual time points *p<0.01; FIG. 16).

Figure 15F:
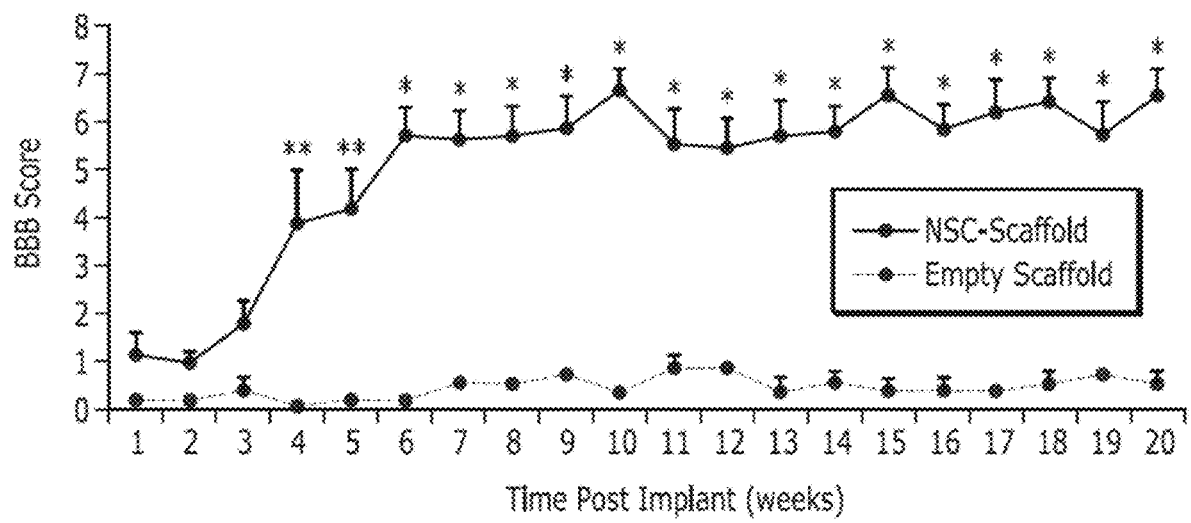

Functional scores reached a mean value of 6.6+0.5 points (+SEM) on the BBB scale in animals that received neural stem cells in implants six months earlier, indicating movement about each joint of the hindlimb, in contrast to a mean score of 0.3+0.2 points in empty implant controls, reflecting inconsistent movements around only one joint (*p<0.01, repeated measures ANOVA; t-test for individual time points and post-hoc Tukey's; FIG. 15F). Formation of neural relays was further investigated via electrophysiological transmission across the complete transection site, by measuring myogenic MEP from the hindlimbs in response to electrical stimulation of the brain (FIG. 15G, FIG. 16A-C).

Figure 15G:
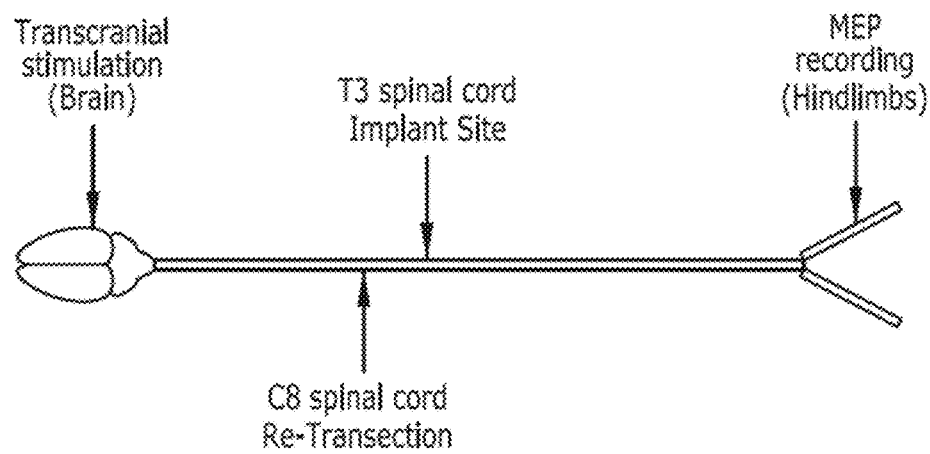
Figure 16A:
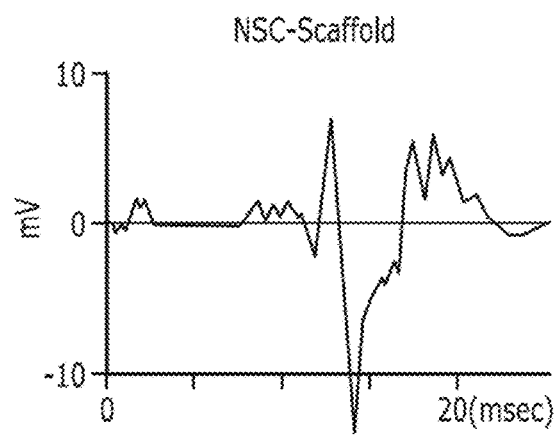
FIG. 16A-D depicts 3D printed implants loaded with neural stem cells, 6 months after implantation. Rats with 3D printed stem cell implants exhibit partial recovery of MEP responses (FIG. 16A). This recovery is abolished by subsequent re-transection of cord above the implant (FIG. 16B). Animals with empty implants show no recovery of MEPs (FIG. 16C).
Figure 16B:
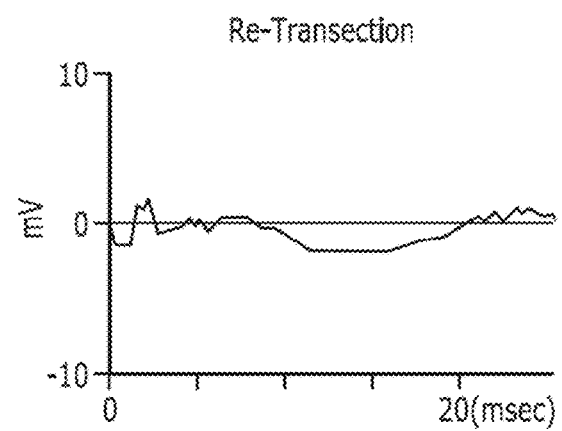
Figure 16C:
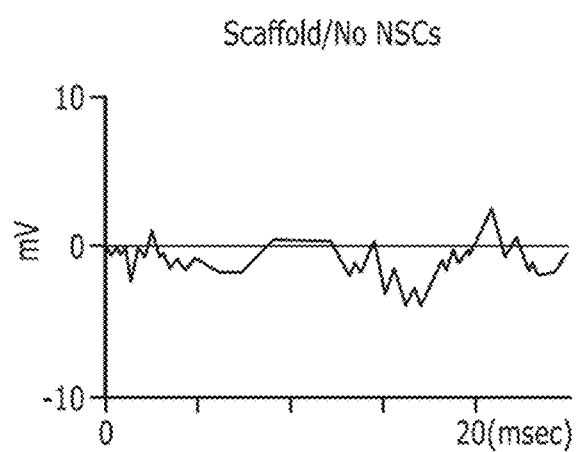
Figure 16D:
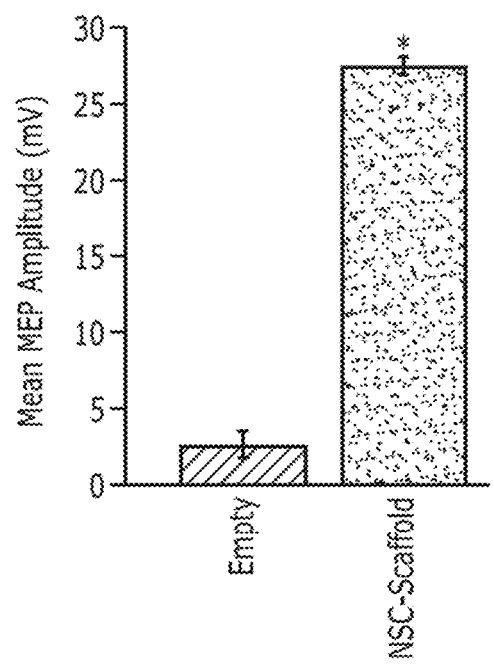

Six months post-injury, rats implanted with 3D biomimetic PEGDA/GelMa implants loaded with neural stem cells exhibited recovery of motor evoked responses, whereas animals implanted with empty implants exhibited responses in the range of baseline noise (p<0.01, t-test; FIG. 15G and FIG. 16D). Re-transection of the spinal cord at C8 level (above the implant site) resulted in loss of all evoked potentials in the hindlimbs (FIG. 16A-C), confirming the formation of new electrophysiological relays across the lesion.

This study demonstrates the use of rapid 3D printing to print biomimetic central nervous system structures. These implants can be readily individualized to specific lesion shapes and lengths. Three-dimensional printed PEGDA/GelMa implants can maintain their structure over at least 26 weeks in vivo. Further, printed implants described can support engraftment of neural stem cells. Further still, printed implants described can support the formation of new synapses. In some embodiments, implants become well vascularized, providing adequate availability of blood, oxygen and nutrients to support consistent cell and axon survival.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A biomimetic nerve or spinal cord implant comprising:
   a three-dimensional (3D) implant body comprising: a first end and a second end formed in a biomimetic shape which mimics structure of a nerve or spinal cord injury site as to host axon organization; and
   a plurality of linear channels within the body originating at the first end and terminating at the second end, wherein the plurality of linear channels within the body mimics host axon organization ex vivo and in vivo, wherein the plurality of linear channels comprise a channel wall thickness up to 100 micrometers,
   wherein the plurality of linear channels retain their pre-implantation structure for at least 4 weeks in vivo, and
   wherein the implant comprises an elastic modulus from about 260 kPa to about 300 kPa.

2. The implant of claim 1, wherein implant is produced by 3D printing.

3. The implant of claim 1, further comprising at least one type of stem cell included in the plurality of linear channels, wherein the at least one type of stem cell is a neural stem cell.

4. The implant claim 3, wherein the neural stem cell is an embryonic stem cell, a iPSC derived stem cell, a directly differentiated neural stem cell, or a combination thereof.

5. The implant of claim 3, wherein the at least one type of stem cell is a mesenchymal stem cell.

6. The implant of claim 3, wherein the stem cell is engineered to express BDNF, NT3, GDNF, or a combination thereof.

7. The implant of claim 1, wherein the implant comprises polyethylene glycol diacrylate or gelatin methacrylol, or a combination thereof.

8. The implant of claim 1, wherein the implant is biomimetic to a spinal cord injury.

9. The implant of claim 1, wherein the implant is biomimetic to a peripheral nerve injury.

10. The implant of claim 1, wherein the plurality of linear channels comprise microchannels.

11. The implant of claim 10, wherein the plurality of linear channels comprise a diameter of about 200 micrometers.

12. The implant of claim 1, wherein the plurality of linear channels are parallel to each other.

13. The implant of claim 1, wherein the plurality of linear channels are configured to guide regenerating axons from the first end to the second end.

14. The implant of claim 1, wherein the plurality of linear channels comprise hexagonal cross-sections clustered as a honeycomb structure.

15. The implant of claim 1, wherein the implant comprises a structure without discrete layers.

16. The implant of claim 15, wherein the implant is composed of a matrix comprising gelatin methacrylate and Poly(ethylene glycol) diacrylate (PEGDA).

17. The implant of claim 16, wherein the plurality of linear channels retain their pre-implantation structure for at least 6 months in vivo.

18. The implant of claim 1, wherein the core comprises gelatin methacrylate, PEGDA, and lithium phenyl-2,4,6-trimethylbenzoylphosphinate.

19. The implant of claim 1, wherein the plurality of linear channels are aligned parallel relative to a host axon and continuously extend from the first end to the second end.

20. The implant of claim 19, wherein the plurality of linear channels are spaced apart by about 66 micrometers.

\* \* \* \* \*